United States Patent
Lightfoot et al.

(10) Patent No.: US 6,329,573 B1
(45) Date of Patent: *Dec. 11, 2001

(54) PLANTS CONTAINING THE GDHA GENE AND METHODS OF USE THEREOF

(75) Inventors: David A. Lightfoot, Carbondale; Lynn M. Long, Murphysboro; Maria E. Vidal Lightfoot, Carbondale, all of IL (US)

(73) Assignee: The Board of Trustees of Southern Illinois University, Carbondale, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/884,235

(22) Filed: Jun. 27, 1997

Related U.S. Application Data

(60) Provisional application No. 60/021,058, filed on Jul. 2, 1996.

(51) Int. Cl.$^7$ .............. C12N 15/82; C12N 5/04; A01H 5/00

(52) U.S. Cl. .......... 800/300.1; 435/418; 435/440; 435/268; 435/410; 435/419; 800/290; 800/295; 800/298; 800/300; 800/306; 800/312; 800/314; 800/320; 800/320.1; 800/320.3

(58) Field of Search .................. 435/418, 440, 435/468, 410, 419; 800/278, 290, 295, 298, 300.1, 300, 306, 312, 314, 320, 320.1, 320.3

(56) References Cited

U.S. PATENT DOCUMENTS 5,998,700 * 12/1999 Lightfoot et al. ............... 800/278

FOREIGN PATENT DOCUMENTS

| 2173730 | 4/1995 | (CA) . |
| 2232542 | 4/1997 | (CA) . |
| WO 95/09911 * | 4/1995 | (WO) . |

OTHER PUBLICATIONS

Wan and Lamaux. Plant Physiol. 1994. vol. 104: 101–105.*
Zaghmout and Torello. J. of Plant Physiolgy. 1992. vol. 140: 101–105.*
Napoli et al. The Plant Cell. 1989. vol. 2: 278–289.*
Della–Cioppa et a. Bio/Technology. 1987. vol. 15: 579–584.*
McPherson and Wooton. Nucleic acid Research. 1983. vol. 11: 5257–5266.*
Gordon–Kamm et al. Plant Cell. 1990. vol. 2: 603–618.*
Loulakakis et al., "Regulation of glutamate dehydrogenase and glutamine synthetase in avocado fruit during development and ripening", Plant Physiol. 106: 217–222 (1994).
Loulakakis et al., "Ammonium–induced increase in NADH–glutamate dehydrogenase activity is caused by de–novo synthesis of the a–subunit", Planta 1987: 322–327 (1992).
Cammaerts and Jacobs, "A study of the role of glutamate dehydrogenase in the nitrogen metabolism of *Arabidopsis thaliana*", Planta 163: 517–526 (1985).
Robinson et al., "The role of glutamate dehydrogenase in plant nitrogen metabolism", Plant Physiol. 95: 509–516 (1991).
Srivastave and Singh, "Role and regulation of L–glutamate dehydrogenase activity in higher plants", Phytochemistry, 26: 597–610 (1987).
Oaks, "Primary nitrogen assimilation in higher plants and its regulation", Can. J. Botany 72: 739–750 (1994).
Joy et al., "Assimilation of nitrogen in mutants lacking enzymes of the glutamate synthase cycle", J. of Exp. Botany, 43: 139–145 (1992).
Stewart et al., "Evidence that glutamate dehydrogenase plays a role in the oxidative deamination of glutamate in seedlings of Zea mays L.", Aust. J. Plant Physiol., 22 000–000 (1995).
Wooton and McPherson, "Genes of nitrate and ammonium assimilation", *The Genetic Manipulation of Plants and its Application to Agriculture*, pp. 89–114 (1984).
McPherson and Wooton, "Complete nucleotide sequence of *Escherichia coli* gdhA gene", Nucl. Acids Res. 11: 5257–5266 (1983).
Windass et al., "Improved conversion of methanol to single–cell protein by *Methylophilus methylotrophus*", Nature 287: 396–401 (1980).
Lightfoot et al., "Expression of the *Escherichia coli* glutamate dehydrogenase gene in the cyanobacterium Synechococcus PCC6301 causes ammonium tolerance", Plant Mol. Biol. 11: 335–344 (1988).
Cao et al., "Ammonium inhibition of Arabidopsis root growth can be reversed by potassium and by auxin resistance mutations aux1, axr1, and axr2(1)", Plant Physiol. 102; 983–989 (1993).
Wang et al., "Ammonium uptake by rice roots", Plant Physiol. 103: 1259–1267 (1993).
Morris et al., "Photorespiratory ammonia does not inhibit photosynthesis in glutamate synthase mutants of Arabidopsis", Plant Physiol. 89: 498–500 (1989).
Lacuesta et al., "Temporal study of the effect of phosphinothricin on the activity of glutamine synthetase, glutamate dehydrogenase and nitrate reductase in *Medicago sativa* L.", J. Plant Physiol. 136: 410–414 (1990).

(List continued on next page.)

*Primary Examiner*—Amy J. Nelson
*Assistant Examiner*—Ousana Zaghmout
(74) *Attorney, Agent, or Firm*—Pillsbury Winthrop LLP

(57) ABSTRACT

Plant nitrogen metabolism in corn and tobacco has been altered by transformation with a highly active assimilatory glutamate dehydrogenase gene. Plants containing the gdhA gene are resistant to phosphinothricin herbicides (PPT) which can include glufosinate herbicides. Additionally, these transformed plants evidence higher levels of tolerance to PPT when combined with another PPT resistant gene. This invention also includes the method of improving plant growth in a field of crops encoding for GDH due to a gdhA transgene.

32 Claims, 21 Drawing Sheets

OTHER PUBLICATIONS

Sakakibara et al., "Isolation and characterization of a cDNA that encodes maize glutamate dehydrogenase", Plant Cell Physiosl. 36: 789–797 (1995).

Magalhaes et al., "Kinetics of $^{15}NH_4^+$ assimilation on Zea mays", Plant Physiol. 94, 647–656 (1990).

Doehlert and Lambert "Metabolic characteristics associated with starch, protein, and deposition in developing maize kernels", Crop Sci. 31:151–157 (1991).

Britton et al., "Structural relationship between the hexameric and tetrameric family of glutamate dehydrogenases", Eur. J. Biochem. 209: 851–859 (1992).

Cock et al., "A nuclear gene with many introns encoding ammonium–inducible chloroplastic NADP–specific glutamate dehydrogenase(s) in *Chlorella sorokiniana*", Plant Nol. Biol. 17: 1023–1044 (1991).

Miller et al., "Alternative splicing of a precursor–mRNA encoding by the *Chlorella sorokiniana* NADP–specific glutamate dehydrogenase gene yields mRNA for precursor proteins of isozyme subunits with different ammonium affinities", Plant Mol. Biol. 37: 243–263 (1998).

Lea, P.J. et al., "The Enzymology and Metabolism of Glutamate, and Asparagine", in Miflin, B.J. and Lea, P.J., eds., *The Biochemistry of Plants,* vol. 16, Chap. 4, pp. 121–159, Academic Press, 1990.

Wootton, J.C. (1983) "Reassessment of ammonium–ion affinities of NADP–specific glutamate dehydrogenases" Biochem. J. 205:527–531.

GenBank listing for "C. sorokiniana NADP–gdh mRNA for NADP–specific glutamate dehydrogenase".

Loulakakis et al. "Regulation of Glutamate Dehydrogenase and Glutamine Synthetase in Avocado Fruit during Development and Ripening." Plant Physiol. 106:217–222 (1994).

Loulakakis et al. "Ammonium–induced increase in NADH–glutamate dehydrogenase activity is caused by de–novo synthesis of the a–subunit." Planta 1987: 322–327 (1992).

Cammaerts and Jacobs. "A study of the role of glutamate dehydrogenase in the nitrogen metabolism of *Arabidopsis thaliana*." Planta 163: 517–526 (1985).

Robinson, et al. "The Role of Glutamate Dehydrogenase in Plant Nitrogen Metabolism." Plant Physiol. 95: 509–516 (1991).

Srivastave and Singh. "Role and Regulation of L–Glutamate Dehydrogenase Activity in Higher Plants." Phytochemistry, vol. 26, No. 3., pp. 597–610 (1987).

Oaks. "Primary nitrogen assimilation in higher plants and its regulation." Can. J. Bot. 72: 739–750 (1994).

Joy, et al. "Assimilation of Nitrogen in Mutants Lacking Enzymes of the Glutamate Synthase Cycle." Journal of Experimental Botany, vol, 43, No. 247, pp. 139–145 (1992).

Stewart, et al. "Evidence that Glutamate Dehydrogenase Plays a Role in the Oxidative Deamination of Glutamate in Seedlings of Zea mays L." Aust. J. Plant Physiol. 22 000–000 (1995).

Wooton and McPherson. "Genes of Nitrate and Ammonium Assimilation". *The Genetic Manipulation of Plants and its Application to Agriculture,* pp. 89–114 (1984).

Wooton and McPherson. "Complete nucleotide sequence of the *Escherichia coli* gdhA gene." Nucleic Acids Research, vol. 11 No. 15 (1983).

Windass, et al. "Improved Conversion of Methanol to single–cell protein by *Methylophilus methylotrophus*." Nature vol. 287 (1980).

Lightfoot, D.A., et al. "Expression of the *Escherichia coli* glutamate dehydrogenase gene in the cyanobacterium Synechococcus PCC6301 causes ammonium tolerance." Plant Molecular Biology 11: 335–344 (1988).

Cao et al. "Ammonium Inhibition of Arabidopsis Root Growth Can Be Reversed by Potassium and by Auxin Resistance Mutations aux1, axr1, and axr2(1)." Plant Physiol. 102: 983–989 (1993).

Wang et al. "Ammonium Uptake by Rice Roots". Plant Physiol. 103, 1259–1267 (1993).

Morris et al. "Photorespiratory Ammonia Does Not Inhibit Photosynthesis in Glutamate Synthase Mutants or Arabidopsis". Plant Physiol. 89, 498–500 (1989).

Lacuesta, M. et al. "Temporal Study of the Effect of Phosphinothricin on the Activity of Glutamine Synthetase, Glutamate Dehydrogenase and Nitrate Reductase in Medicago sativa L." J. Plant Physiol. vol. 136, pp. 410–414 (1990).

Sakakibara, et al. "Isolation and Characterization of a cDNA That Encodes Maize Glutamate Dehydrogenase". Plant Cell Physiol. 36(5): 789–797 (1995).

Magalhaes, et al. "Kinetics of 15NH4+ Assimilation on Zea mays", Plant Physiol. 94, 647–56 (1990).

Doehlert, D.C. and Lambert, R.J. "Metabolic Characteristics Associated with Starch, Protein, and Oil Deposition in Developing Maize Kernals." Crop Sci. 31:151–157 (1991).

* cited by examiner

E.coli gdhA

```
1
TCGAAAACTGCAAAGCACATGACATAAACAACATAAGCACAATCGTATTAATATATAAGGGTTTTATA

TCTATGGATCAGACATATTCTCTGAGTCATTCCTCAACCATGTCCAAAAG

CGCGACCCGAATCAAACCGAGTTCGCGCAAGCCGTTCGTGAAGTAATGACCACACTCTGGCCTTTCTT

GAACAAAATCCAAATATGCGCCAGATGTCATTACTGGAGCGTCTGGTTGAA

CCGGAGCGCGTGATCCAGTTCGCGGTGTATGGGTTGATGATCGCAACCAGATACAGGTCAACCGTGCAT

GGCGTGTGCAGTTCAGTTCGCTGCCATCGCCCGTACAAAGGGGTATGCGC

TTCCATCCGTCAGTTAACCTTTCATTCTCAAATTCCCGGCTTGAACAAACCTTCAAAAATGCCCTGA

CTACTCTGCCGATGGGGGTGGTAAAGCGGCAGCGGATTTCGATCCGAAA

GGAAAAAGCGAAGGTGAAGTGATGCGTTTTGCCAGGCTGATGACTGAACTGTATGCCACCTGGGCG

CGGATACCGAGCGTTCCGGCAGGTGATATGGGGTTGGTGTCGTGAAGTC
```

Fig. IA

GGCTTTATGGGGGATGATGAAAAGCTCTCCAACAATACCGCCTGCTCTTCACCGGTAAGGGCCTTT

CATTTGGGCCAGTCTTATTCGCCCGGAAGCTACGCGGCTACGGTCTGGTT

TATTTCACAGAAGCAATGCTAAAACGCCACGGTATGGGTTTGAAGGATGCGGTTTCCGTTTCTGGCT

CCGGCAACGTCGCCCAGTACGCGCTATCGAAAAAGCGATGGAATTTGGTGCT

CGTGTGATCACTGGTCAGACTCCAGCGGCACTGTAGTTGATGAAAGCGGATTCACGAAAGAGAAACTGGC

ACGTCTTATCGAAATCAAAGCCAGCCGCGATGGTCGAGTGGCAGATTAC

GCCAAAGAATTTGGTGTCTATCTCGAAGGCCAACAGCCCTGTCTCTACCGGTGATATCGCCCTGCCT

TGCGCCACCCAGAATGAACTGGATGTTGACGCGGCATCAGCTTATC

GCTAATGGCGTTAAAGCCGTCGCCGAAGGGCAAATATGCCGACCACCATGAAGCGACTGAACTGTTCCAG

CAGGCAGGCGTACTATTTGCACCGGGTAAAGCGGCTAAATGCTGGTGGC

*Fig. 1B*

GTCGCTACATGGGCCTGGAAATGGCACAAAACGCTGCGGCCTGGCCTGGAAAGCCGAGAAAGTTGACGCA

CGTTTGCATCACATCATGCTGGATATCCACCATGCCTGTGTTGACCAT

GGTGGTGAAGGTGAGCAAACCAACTACGTGCAGGGGCGCAACATGCCGGTTTGTGAAGGTGCCGATGCG

ATGCTGGCGCAGGGTGTGATTTAAGTGTAAATGCCTGATGGCGTAC

GCTTATCAGGCCTACAAATGGGCACAATTCATTGCAGTTACGCTCTAATGTAGGCCCGGCCAAGCCGAGGCC

CCCGGCAAAATTTCAGGCGGTTTATGAGTATTTAACGGATGATGCTCCC

CACGGAACATTTCTATGGGCCAATTTCTACTGTAGTGCTCCCAAAACTGCTGTGTCGTAACGATAA

CACGCTTCAAGTTCAGCATCCGTTAAC

Forward primer at 5'

<u>XbaI</u>   <u>Kozak</u>
5'-...G GGT TCT AGA ACA ATG GAT CAG ACA TAT TCT CTG GAG...3'
                        start
                        codon 5'-...G GGT TTT ATA TCT ATG GAT CAG ACA TAT TCT CTG GAG TCA TTC CTC AAC-gdhA
3'-...C CCA AAA TAT AGA TAC CTA GTC TGT ATA AGA GAC CAC AGT AAG GAG TTC-gene
........ M   D   Q   T   Y   S   L   E   S   F   L   N

Fig. 2B

Reverse primer at 3' stop    mRNA
                            codon  destabilizer
gdhA--T GCG CTG GCG CAG GGT GAG ATT TAA GTT GTA AAT G...-3'
gene--C CGC GAC CGC GTC CCA CTC TAA ATT CAA CAT TTA C...-5'
........A   M   L   A   Q   G   V   I 3'...C TAC GAC CGC GTC CCA CAC TAA ATT <u>CTC GAG</u> TTA C...5'
                                         SacI METAspGlnThrTyrSerLeuGluSerPheLeuAsnHisValGlnLysArgAspProAsn
GlnThrGluPheAlaAlaGlnAlaValArgGluValMETThrLeuTrpProPheLeuGlu
GlnAsnProLysTyrArgGlnMETSerLeuLeuArgLeuValGluProGluArgVal
IleGlnPheArgValValTrpValAspAspArgAsnGlnIleGlnValAsnArgAlaTrp
ArgValGlnPheSerSerAlaIleGlyProTyrLysGlyGlyMETArgPheHisProSer
ValAsnLeuSerIleLeuLysPheLeuGlyPheGluGlnThrPheLysAsnAlaLeuThr
ThrLeuProMETGlyGlyGlyGlyLysGlyGlySerAspPheAspProLysGlyLysGlu
GlyGluValMETArgPheCysGlnAlaLeuMETThrGluLeuTyrArgHisLeuGlyAla
AspThrAspValProAlaGlyAspIleGlyValGlyGlyArgGluValGlyPheMETAla
GlyMETMETLysLysLeuSerAsnAsnThrAlaCysValPheThrGlyLeuValPheThrGlu
PheGlyGlySerLeuIleArgProGluAlaThrGlyTyrLeuValTyrPheGlyLeuSer
AlaMETLeuLysArgHisGlyMETGlyPheGluGlyMETArgValSerValSerGlySer
GlyAsnValAlaGlnTyrAlaIleGluLysAlaMETGluPheGlyAlaArgValIleThr
AlaSerAspSerGlyThrValValAspSerGlyPheThrLysGluLysLeuAla
ArgLeuIleGluIleLysAlaSerArgAspGlyArgValAlaAspTyrAlaLysGluPhe
GlyLeuValTyrLeuGlyGlnProTrpSerLeuProValAspIleAlaLeuPro
CysAlaThrGlnAsnGluLeuGlyAspValAspAlaAlaHisGlnLeuIleAlaAsnGlyVal
LysAlaValAlaGlyValLeuPheAlaProGlyLysAlaAsnAlaGlyValAlaThrSer
GlnLeuGluMETAlaGlnAsnAlaAlaArgLeuGlyTrpLysAlaCysValAspHisGlyGluGly
GlyLeuHisIleMETAlaAspIleHisAlaCysValAspHisGlyGlyGly
ArgLeuGlnThrAsnTyrValGlnGlyAlaAsnIleAlaGlyPheValLysValAlaAspAla
METLeuAlaGlnGlyValIle

Fig. 3

Mutagenized gdhA for Plant expression (tobacco and corn)

XbaI Kozak
5'- TCTAGAACAATGGATCAGACATATTCTCTGGAGTCATTCCTCAACCATGTCCAAAAG

CGCGACCCGAATCAAACCGAGTTCGGCCAAGCCGTTCGTGAAGTAATGACCACACTCTGGCCTTTTCTT

GAACAAATCCAAATATGCCAGATGTCATTACTGGAGCGTCTGGTGAA

CCGGAGCGGGTGATCTCCAGTTTCGCGGTGGATGATCGCAACCAGATACAGTTCAACCGTGCAT

GGCGTGTGCAGTTCAGCTCTGCCATGGCCCGTACAAAGGCGTATGCGC

TTCCATCCGTCAGTTAACCTTTCCATTCTCAAATTCCTCGCTTTGAACAACCTTCAAAAATGCCCTGA

CTACTCTGCCGATGGGCGGTGTAAAGGCGGCAGCGATTTCGATCCGAAA

GGAAAAGCGAAGGTGAAGTGATGCGTTTTTGCCAGGCGCTGATGACTGAACTGTATGCCCACCTGGGCG

CGGATACCGACGTTCCGGCAGGTGATATGCGGGGTTGGTGTCGTGAAGTC

Fig. 6AI

GGCTTTATGGCGGGGATGATGAAAAGCTCTCCAACAATACCGCCTGCTCTTCACCGGTAAGGGCCTTT

CATTTGGGCGCAGTCTTATTCGCCCGGAAGCTACCGGCTACGGTCTGGTT

TATTTCACAGAAGCAATGCTAAAACGCCACGGTATGGGTTTGAAGGGATGCCGTTTCCGTTTCTGGCT

CCGGCAACGTCGCCCAGTACGCTATGCGAAAAAGCGATGGAATTTGGTGCT

CGTGTGATCACTGGTCAGACTCCAGCGGGCACTGTAGTTGATGAAGCGGATTCACGAAAGAGAAACTGGC

ACGTCTCTATCGAAATCAAAGCCAGCCGCGATGGTCGAGTGGCAGATTAC

GCCAAAGAATTTGGTCTGTCTATCTCGAAGGCCAACAGCCGTGTCTCTACCGGTTGATATCGCCCTGCCT

TGCGCCACCCAGAATGAACTGGATGTTGACGCGGCCATCAGCTTATC

GCTAATGGCGTTAAAGCCGTCGCCGAAGGGCAAATATGCCGACCACCATCGAAGGCGACTGAACTGTTCCAG

CAGGCAGGCGTACTATTTGCACCGGGCTAAAGCGGCTAATGCTGGTGGC

GTCGCTACATCGGGCCTGAAATGCCACAAAACGCTGCGCCTGCTGGCTGAAAGCCGAGAAAGTTGACGCA

*Fig. 6A2*

```
CGTTTGCATCACATCATGCTGATATCCACCATGCCTGTGTTGACCAT
GGTGGTGAAGGTGAGCAAACCAACTACGTGCAGGGCGCGAACATTGCCGGTTTTGTGAAGGTTGCCGATGCG
ATGCTGGCGCAGGGTGTGATTTAAGTTGTAAATGCCTGATGGCTAC
GCTTATCAGGCCTACAAATGGGCACAATTCATTGCAGTTACGCTCTAATGTAGGCCCGGGCAAGGCGCAGGCC
CCCGGCAAATTTCAGGCGTTTATGAGTATTTAAGAGCTC
          SacI
```

*Fig. 6A3*

Mutagenized gdhA for chloroplast targetting (tobacco and corn)

1
SphI
-----
gCATgCATCAGACATATTCTCTGGAGTCATTCCTCAACCATGTCCAAAAG

CGGGACCCGAATCAAACCGAGTTCGCGCAAGCCGTTCGTGAAGTAATGACCACACTCTGCCCTTTTCTT

GAACAAATCAAAATATCGCCAGATGTCATTACTGGAGCGTCGGTTGAA

CCGGAGCGCGTGATCCAGTTTCGGTGTATGGTTGATGATCGCAACCAGATACAGTCAACCGTCAT

GGCGTGTGCAGTTCAGCTCTGCCCCTGCCATCGGCCCGTACAAAGGCGTATGCGC

TTCCATCCGTCAGTAACCTTTCCATTCTCAAATTCCTGGCTTTGAACAAACCTTCAAAAATGCCCTGA

CTACTCTGCCGATGGGCGGTGTAAAGGCGGCAGCGATTTCGATCCGAAA

GGAAAAGGCGAAGGTGAGTGATGCGTTTTTGCCAGGCGTGATGACTGAACTGTATCGCCACCTGGGCG

CGGATACCGACGTTCCGGCCAGTGATATCGGGGTTGGTGTCGTGAAGTC

*Fig. 6BI*

GGCTTTATGGGGGATGATGAAAAGCTCTCCAACAATACCGCCTGGTCTTCACCGGTAAGGCCTTT

CATTTGGGGCAGTCTTATTCGCCCGGAAGCTACCCGGCTACGGTCTGGTT

TATTTCACAGAAGCAATGCTAAAACGCCACGGTATGGGTTTGAAGGATGCCGTTCCGTTTCTGGCT

CCGGCAACGTCGCCCAGTACGCTATCGAAAAGCGATGAATTTGGTGCT

CGTGTGATCACTGCGGTCAGACTCCAGCGGGCACTGTAGTTGATGAAGCGGATTCACGAAGAGAAACTGGC

ACGTCTTATCGAAATCAAAGCCAGCCGCGATGGTCGAGTGGCAGATTAC

GCCAAAGAATTTGGTCTCGGTCTATCTCGAAGGCCAACAGCCCGTGTCTCTACCGGTTGATATCGCCCTGCCT

TGCGCCACCCAGAATGAACTGGATGTTGACGCCGCATCAGCTTATC

GCTAATGCGTTAAAGCCCGTCGCCGAAGGGCAAATATGCCGACCACCATCGAAGCGACTGAACTGTTCCAG

CAGGCAGGCGTACTATTTGCACCGGGTAAAGCGGCTAATGCTGGTGGC

*Fig. 6B2*

```
GTCGCTACACATCGGGGCCTGGAAATGGCACAAAACGCTGCGCCTGGGCCTGGAAAGCCGAGAAAGTTGACGCA

CGTTTGCATCACATCATGCTCGATATCCACCATGCCTGTGTTGACCAT

GGTGGTGAAGGTGAGCAAACCAACTACGTGCAGGGCGCGAACATTGCCGGTTTTGTGAAGGTGCCGATGCG

ATGCTGGGGCGCAGGGGTGTGATTTAAGTTGTAAATGCCTGATGGGCTAC

GCTTATCAGGCCTACAAATGGGCACAATTCATTGCAGTTACGCTCTAATGTAGCCCGGCAAGCCGCAGCGCC

CCCGGCAAATTTCAGGCGTTTATGAGTATTTAAGAGCTC
                                  SacI
```

*Fig. 6B3*

Mutagenized gdhA for Plant expression with added linker restriction sites (corn)

PstI SalI XbaI Kozak
ctgcaggtcgacTCTAGAACAATGGATCAGACATATTCTCGGAGTCATTCCTCAACCATGTCCAAAAG

CGGGACCCGAATCAAACCGAGTCGGCAAGCCGTTCGTGAAGTAATGACCACACTCTGGCCTTTCTT

GAACAAATCCAAAATATCGCCAGAGTGTCATTACTGGAGCGTCTGGTTGAA

CCGGAGCGCGTGATCCAGTTTCGGTGGTGTATGGGTTGATGATCGCAACCAGATACAGGTCAACCGTGCAT

GGCGTGTGCAGTTCAGCTCTGCCATCGCCCGTACAAAGGCGGTATGCGC

TTCCATCCGTCAGTTAACCTTTCCATTCTCAAATTCCTCGGCTTTGAACAAACCTTCAAAAATGCCCTGA

CTACTCTGCCGATGGGCGGTGGTAAAGGGCAGCGATTTCGATCCGAAA

GGAAAAGGCGAAGGTGAAGTGATGCGTTTTGCCAGCGCTGATGACTGAACTGTATCGCCACCTGGGCG

CGGATACCGACGTTCCGGCAGGTGATATCGGGTTGGTGTCGTGAAGTC

Fig. 7AI

```
GGCTTTATGGCGGGATGATGAAAAGCTCTCCAACAATACCGCCTGCGTCTTCACCGGTAAGGCCTTT

CATTTGGCGGCAGTCTTATCGCCCGAAGCTACCGGTCTCTGGTT

TATTTCACAGAAGCAATGCTAAAACGCCACGGTATGGGTTTTGAAGGGATGCGCGTTTCCGTTTCTGGCT

CCGGCAACGTCGCCCAGTACGCTATCGAAAAAGCGATGGAATTTGGTGCT

CGTGTGATCACTGGCTTCAGACTCCAGCGGCACTGTAGTTGATGAAAGCGGATTCACGAAAGAGAAACTGGC

ACGTCTTATCGAAATCAAAGCCAGCCGCGATGGTGAGTGGCAGATTAC

GCCAAAGAATTGGTCTGTCTATCTCGAAGGCCAACAGCCGTGTCTCTACCGGTGATATGCCCTGCCT

TGCGCCACCCAGAATGAACTGGATGTTGACGCCGCATCAGCTTATC

GCTAATGGCGTTAAAGCCGTCGCCGAAGGGCAAATATGCCGACCACCATCGAAGCGACTGAACTGTTCCAG

CAGGCAGGCGTACTATTTGCACCGGGTAAAGCGGGTAATGCTGGTGGC
```

*Fig. 7A2*

```
GTCGCTACACATCGGGAAATGGCACAAAACGCTGCGCCTGGCTGGAAGCCGAGAAAGTTGACGCA

CGTTTGCATCACATCATGCTGGATATCCACCATGCCTGTGTTGACCAT

GGTGGGTGAAGGTGAGCAAACCAACTACGTGCAGGGGCGAACATTGCCGGTTTTGTGAAGGTTGCCGATGCG

ATGCTGGCGCAGGGTGTGATTTAAGTTGTAAATGCCTGATGGCGTAC

GCTTATCAGGCCTACAAATGGGCACAATTCATTGCAGTTACGCCTCTAAATGTAGGCCCGGGGCAAGCGCAGCGCC

CCCGGCAAAATTTCAGGCGTTTATGAGTATTTAAGAGCTC
                                    SacI
```

*Fig. 7A3*

```
EcoRI      SphI
5' aattcgaaccccttcgcatg 3'
3'     gcttggggaagc     5'
```

3' EcoRI SphI adapter - between nosT and plasmid for corn transformation

Fig. 8

PLANTS CONTAINING THE GDHA GENE AND METHODS OF USE THEREOF

This application is copending and claims the priority from U.S. provisional application, 60/021,058 having a Jul. 2, 1996 filing date.

FIELD OF THE INVENTION

The present invention relates to plants transformed with the gdhA gene. More specifically, the present invention relates to a gene which can be used as a selectable marker in transformation. Additionally, the present invention relates to a dual gene herbicide resistance and tolerance package that includes the phosphinothricin acetyl transferase (PAT) gene and/or the Bar gene in combination with the gdhA gene.

BACKGROUND OF THE INVENTION

Plants utilize nitrogen to form organic compounds. Ammonia and ammonium ions do not accumulate in plant cells but instead are rapidly assimilated. Ammonium assimilates through two possible pathways. The first pathway produces glutamate and is catalyzed by glutamate dehydrogenase (GDH), which is found in chloroplasts and mitochondria.

The second pathway for assimilation of ammonia involves a reaction with glutamate to form its amide, glutamine. This reaction is catalyzed by glutamine synthase (GS) and requires energy in the form of ATP. Glutamine is then catalyzed by glutamate synthase (GOGAT) to form glutamate. GS appears in chloroplasts and cytosol in leaves and roots, whereas, GOGAT is in leaf chloroplasts and plastids in roots.

Although both pathways result in glutamate, the second pathway appears more important in ammonium assimilation in plants. Glutamate dehydrogenase, the enzyme of the first pathway, has a high Km value. This value which is the concentration of ammonia where half of the enzyme maximum operation rate is within levels which are toxic for plant cells. In contrast, the GS Km value is much lower. Additionally, radioactive labeling of $NO_3$ or $NH_4$ show labeled nitrogen in the amide group of glutamine first.

Although GS has a high affinity for ammonia and GDH has a lower affinity, GS has low specific activity per enzyme molecule and GDH has high specific activity per molecule.

Ammonium assimilation pathways of plants and microorganism; although maybe not fully understood; have been known. In October of 1980, the ICI Agricultural Division published in *Nature*, Volume 287, page 396 an article on improved conversion of methanol to single cell protein by *Methylophilus methylotropus*.

The researchers cloned the glutamine dehydrogenase gene of *Escherichia coli* (*E. coli*) into a mutant of *Methylophilus methylotropus* organism that lacks GOGAT. The paper explained that the GDH pathway should result in the organism consuming less energy. The researchers speculate that potential industrial or agricultural savings could be made by identification of features that incur "energy penalty" and this is an exciting area for recombinant DNA. This organism to organism transfer of the *E. coli* GDH gene should substantially decrease in enzyme activity thus a plasmid with a high copy number was used.

In 1988, the expression of *E. coli* glutamate dehydrogenase in cyanobacterium was reported in *Plant Molecular Biology*, Volume II, pages 335–344. Cyanobacterium that lacked glutamate dehydrogenase were transformed with the gdhA gene of *E. coli* and levels of NADP-specific glutamate dehydrogenase activity resulted in the transformed microorganism. The authors speculate that it would be interesting to investigate the engineering of glutamate dehydrogenase activity to higher plants and to study in detail the possible roles for glutamate dehydrogenase activity in ammonium detoxification.

Although there was some speculation on nitrogen assimilation genes in higher plants, in a paper on nitrogen assimilatory genes in *The Genetic Manipulation of Plants and its Application to Agriculture*, at page 109, the authors state that it would be tempting to suggest that crop plants might show increased metabolic efficiency if ammonium assimilation was channeled through glutamate dehydrogenase. But the authors clearly list the number of technological barriers to this. There remained a number of barriers to this research including the potential negative consequences of uncontrolled expression in the plant. The authors reluctantly conclude "perhaps" there may be some benefit in replacing glutamate synthase, with ammonium—utilizing alternatives.

In *Molecular and General Genetics* in 1993 in volume 236, pages 315–325, the modulation of glutamine synthetase gene expression in tobacco was reported. An alfalfa gene was placed in the tobacco plant cells in the sense and antisense position. Partial inhibition in the antisense position was seen without a true homologous gene.

In 1994, it was reported that increasing the activity of plant nitrogen metabolism enzymes may alter plant growth, development and composition. Increased yield and protein content as well as reduced levels of nitrogen in agricultural runoff water and food may result. Plant nitrogen metabolism has been altered by transformation with a highly active assimilatory bacterial glutamate dehydrogenase gene, plant glutamate dehydrogenase is less active in ammonium gene has been altered by PCR and PCR strand overlap exchange to modify coding region and allow high levels of expression in plant cells. The 5' non-coding region has been altered to increase translation and permit protein targeting to either cytosol or chloroplasts. The 3' non-coding region has been altered to stabilize the mRNA and ensure appropriate polyadenylation of the mRNA. Certain codons likely to inhibit expression to high levels in plant cells have been altered. The effects of the various sequence substitutions on gene expression in plant cells compared to the unmodified gene will be reported. This abstract is reporting on speculation of the researchers as the abstract clearly reference what may happen or codons that are likely to inhibit. The abstract appears to provide a guess as to what might happen, not something that has been done.

Although researchers speculated that the gdhA gene may be useful in higher plants, the drawbacks and possible disruption of the photosynthesis pathway lead researchers to the belief that the potential use was probably not possible due to technical barriers. Even the inventor was only speculating on the potential of the gdhA gene to avoid ammonia toxification.

There remains a need to transform cereals to determine if the gdhA gene would have any effect on the plant in either nontoxifying levels or toxic levels of ammonia. The usefulness of the gene as a tolerance mechanism for certain herbicides was not proven prior to this. This gene is tolerant to phosphinothricin which can include glufosinate and other similar herbicidally active derivatives, salts, and acids thereof. The combination of this gdhA gene with other selectable markers to increase plant resistance to herbicide damage was heretofore undiscovered. The ability of a plant to increase dry weight due to increased nitrogen uptake in even nontoxic levels of ammonia was not realized or considered until the present invention.

The composition of proteins, sugars, starch, cellulose and structural lipids, storage lipids and oils can be altered by increasing or decreasing nitrogen supply to the plant. The question remains if the supply of nitrogen is at a high level can the composition of proteins, sugars, starch, cellulose, lipids and oils be modified by the addition of the gdhA gene. The present invention clearly indicates that the protein content in seeds and leaves is altered. Although the gdhA gene may have had some suggested potential to assimilate additional nitrogen in highly toxic nitrogen conditions, the gdhA genes result GDH enzyme has a weaker ammonium affinity than the ATP specific GS. At lower ammonium concentrations assimilation by GDH was expected to be limited due to its lower ammonium affinity and the reversibility of its reaction. Thus, it was surprising and unexpected that the gdhA gene when in a plant produced measurable changes in the number of leaves and protein content of the leaves and the seeds, the dry weight of the plant even in soils having normal ammonium levels. At these levels, the expectation would be that the GS/GOGAT cycle would be the active cycle.

SUMMARY OF THE INVENTION

An object of this invention is to provide transformed plants containing the gdhA gene that evidences increased plant biomass.

Another object of this invention is to provide transformed plants that increases leaf size.

Still another object of this invention is to provide transformed corn plants that are resistant to PPT.

Yet a different object of this invention is to provide a corn plant with dual gene resistance to PPT in the GS and the GDH pathways.

Furthermore, an object of the present invention is to provide altered plant growth and yield in seed crops including sunflower, corn, soybeans and canola (brassica).

Additionally, the object of the present invention is to provide a gdhA transformed corn plant that contains a gene that alters the composition of the makeup of the corn seed.

Broadly, then the present invention includes a method of improving crop growth by applying to a field containing a crop, which are phosphinothricin resistant due to having an expressible transgene encoding for phosphinothricin resistant glutamate dehydrogenase enzyme, a sufficient amount of a phosphinothricin class herbicide to control undesirable vegetation without significantly affecting crop growth.

This method includes a gene which is mutagenized, and a gene which is a modified bacterial gene. The gene can contain the Kozac consensus sequence in a particular embodiment. This method, of course, can include instances where the phosphinothricin class herbicide is combined with a second herbicide and then applied to the transformed crop.

The method includes transformed crops which are selected from the group consisting of corn, cotton, brassica, soybeans, wheat or rice. Some of these crops are naturally resistant and the addition of the gdhA allows additional heartiness during herbicide application.

This invention is not just about the method described about. This invention also includes within its broad scope. Transgenic plant cells and progeny having expression cassettes with a transcription initiation region functional in the plant cells, a DNA sequence that encodes for the GDH enzyme in said plant cells, and a transcription termination region functional in the plant cells. The expression cassette then imparts to the plant a detectable level of herbicide resistance to the phosphinothricin class of herbicides.

In the cells at least one of the transcription region or the termination region is not naturally associated with the gdhA sequence. The invention encompass these cells wherein the sequence is from a bacterial gene preferably from $E.\ coli$. In some embodiments these cells, including a sequence from the bacterial gene, are modified to enhance expression in plant cells. The cells, plants and progeny include a DNA sequence that encodes the amino acid sequence shown in FIG. 3.

To enhance amino acid production, the cells can include a chloroplast transient peptide adapted to target the chloroplasts. In other embodiments, cells have a transcription initiation region which is constitutive in action or can be organ or tissue specific.

The present invention includes cell culture of cells that contain a marker gene that is capable of growth in a culture medium which includes a herbicide which is in the phosphinothricin class. The herbicide includes bialaphos, LIBERTY glufosinate, and IGNITE glufosinate. Additionally, the present invention includes a cell culture of cells having a gene resistant to the PPT and a marker gene that is capable of growth in a culture medium which includes a herbicide which is not a phosphinothricin class herbicide.

The invention includes a transgenic plant originally formed from nontransgenic plants and progeny thereof which contains an expression cassette having a transcription initiation region functional in the plant cell, a genetically engineered DNA sequence that is capable of encoding for the GDH enzyme in the plant cells wherein the plant evidences detectable alteration in GDH activity when compared to the nontransgenic plants like that from which the transgenic plant was formed. The alteration in GDH activity could be increased activity or decreased activity. The transgenic plant can be a dicot or a monocot. Of particular interest are transgenic $Zea\ mays$ plants. Alternatively, the transgenic plant can be selected from a group consisting of brassica, cotton, soybeans, and tobacco. The change in the nitrogen assimilation pathway allows other parts of the plant to be altered.

The invention includes a transgenic plant that forms seeds and has genetically engineered DNA sequences that alters the oil content of the seed of the plant and evidences altered GDH activity when compared to a transgenic plant containing only the oil altering DNA sequence.

The invention covers a transformed corn plant containing a bacterial glutamate dehydrogenase gene. Additionally, this plant can contain a second gene that was introduced into the plant or its ancestors by genetic engineering that is resistant to PPT.

The invention broadly covers a recombinant plasmid characteristic in that the recombinant plasmid contains a constitutive promoter, a chloroplast transit peptide and the bacterial gdhA gene and a transcriptional termination region. A biologically pure culture of a bacterium characterized in that the bacterium is transformed with the recombinant plasmid.

BRIEF DESCRIPTION OF THE DRAWINGS

FIG. 1 shows the DNA sequence of the gdhA gene (SEQ ID NO:1) of $E.\ coli$.

FIG. 2 shows the forward primer (panel A, SEQ ID NO:3) at 5' and the reverse primer (panel B, SEQ ID NO:4) at 3' of the non-coding regions (panel A, SEQ ID NOS:5–7, panel B, SEQ ID NOS:8–10) of the gdhA gene.

SacI and XbaI restriction enzyme sites are indicated as is the sequence modification to introduce Kozac's consensus sequence (double underline). The bold portion was eliminated as an in RNA destabilizing sequence.

FIG. 3 shows the amino acid sequence (SEQ ID NO:11) of E. coli GDH enzyme expressed in both the tobacco and corn.

Figure 4:
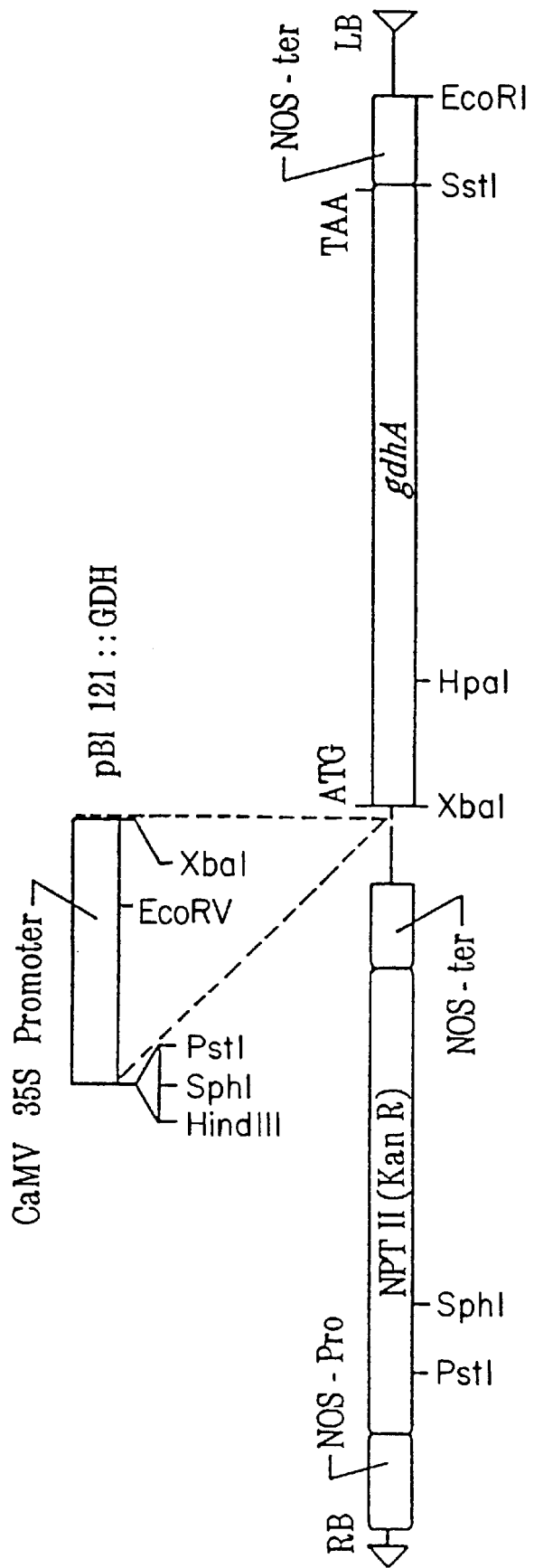

FIG. 4 shows a linear map of the plasmid vector pBI121:GDH1 developed in Example I. The plasmid has the uidA gene removed and the gdhA gene inserted.

Figure 5:
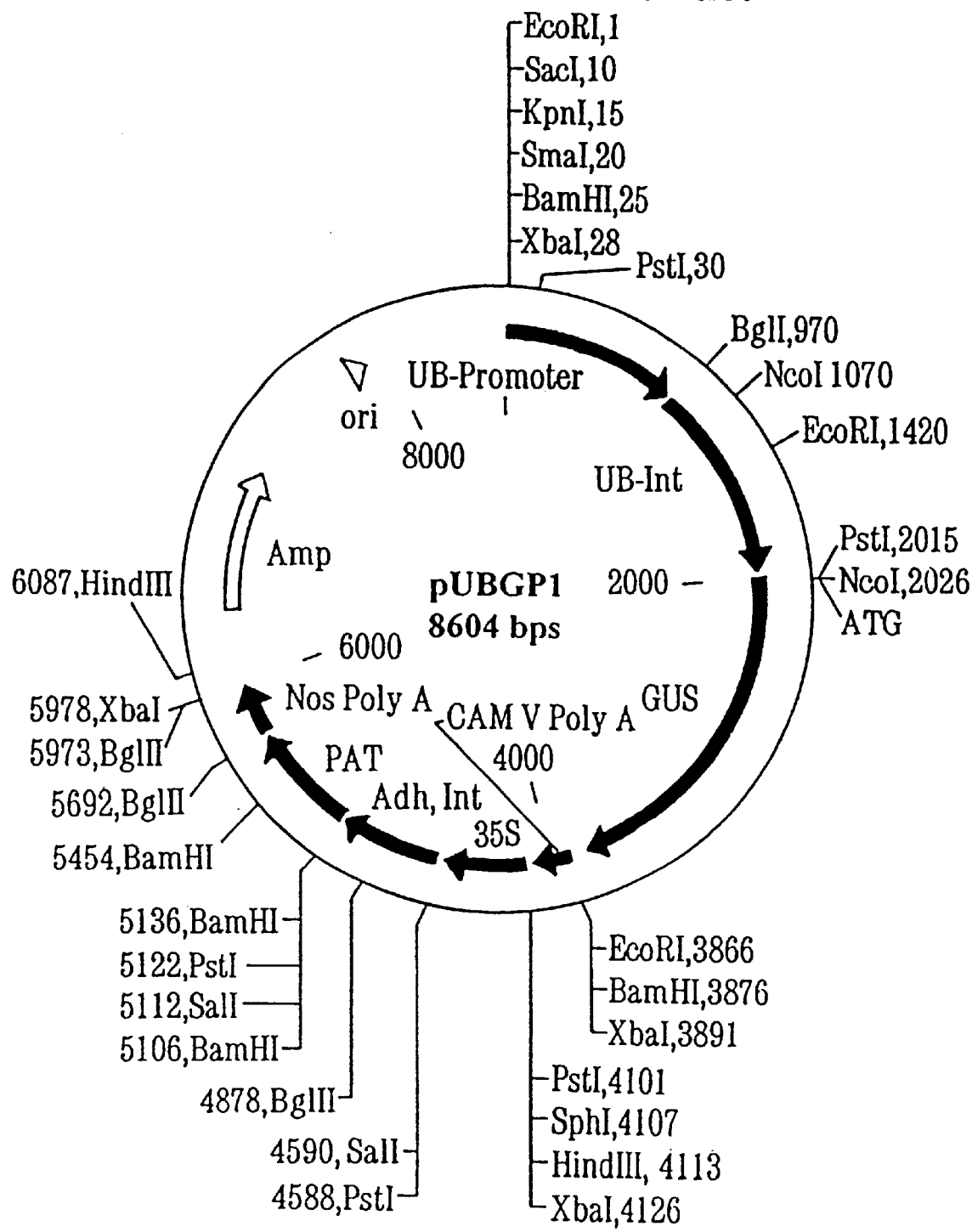

FIG. 5 shows a circular map of the plasmid vector pUBGP1 used in the examples as starting material and a control for plasmids useful in Zea mays.

FIG. 6A shows the DNA (SEQ ID NO:12) sequence of the mutagenized gdhA gene used for plant expression (tobacco and corn).

FIG. 6B shows the DNA sequence (SEQ ID NO:13) including the SphI site of the mutagenized gdhA gene used for plant expression (tobacco and corn).

FIG. 7A shows the mutagenized gdhA gene (SEQ ID NO:14) with the added restriction sites for use in Zea mays.

Figure 7B:
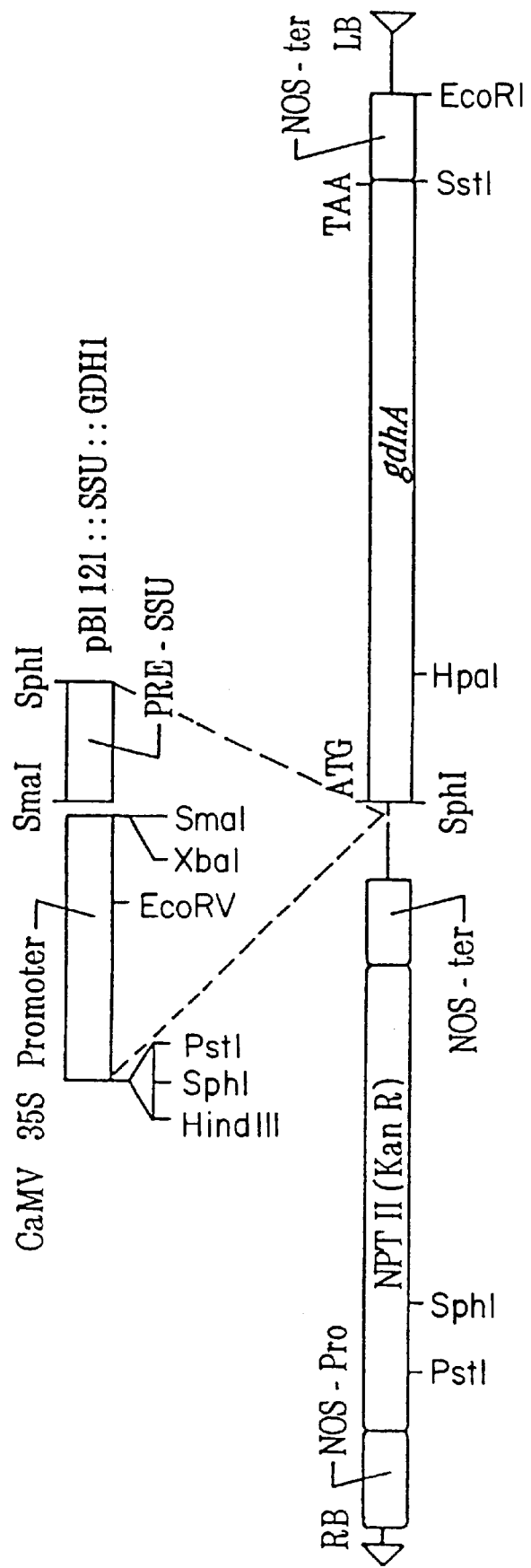

FIG. 7B shows a linear plasmid map of pBI 121::SSU::GDH1.

FIG. 8 shows the 3' EcoRI SphI adapter (SEQ ID NOS:15–16) between nosT and plasmid for corn transformation.

Figure 9:
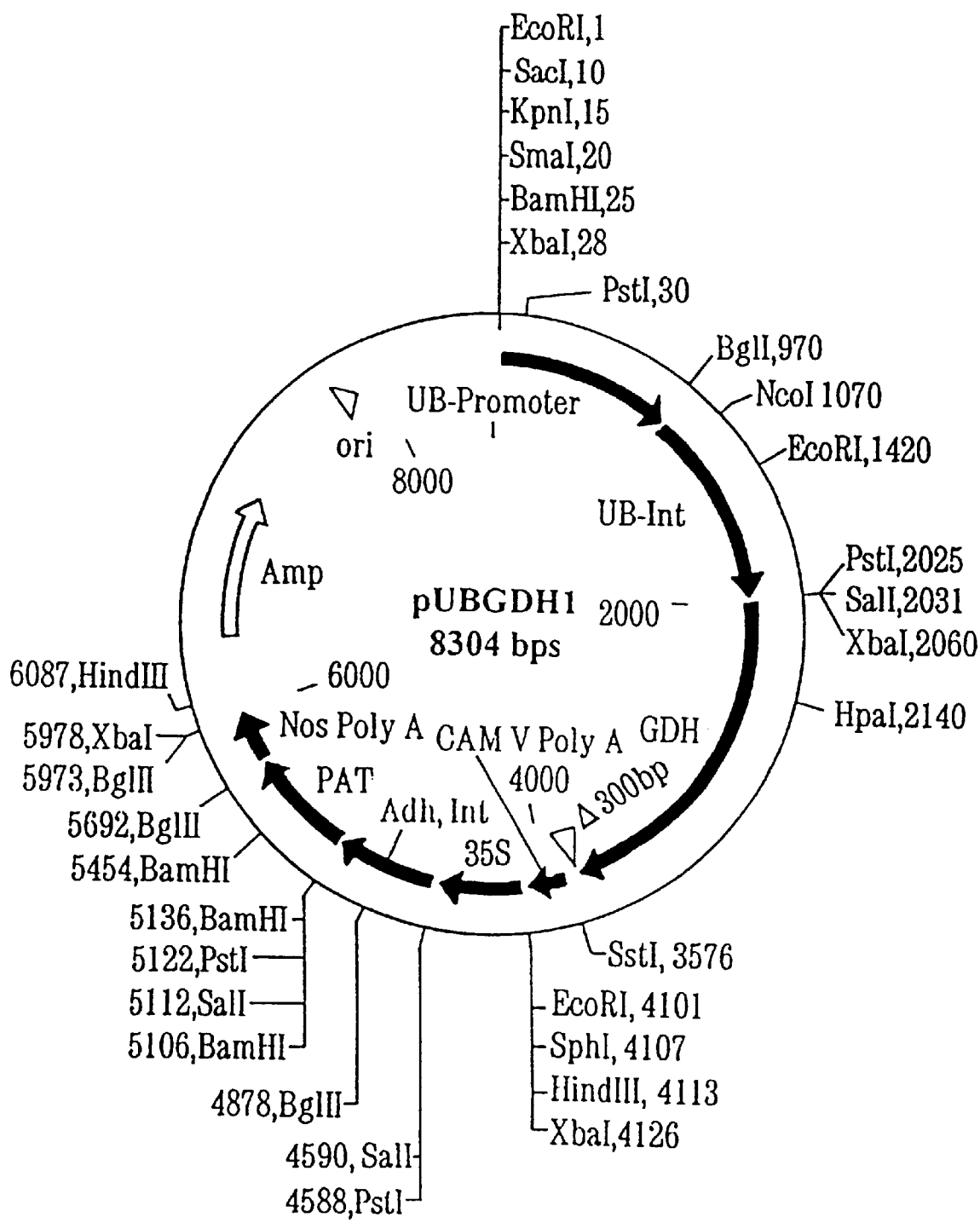

FIG. 9 shows a circular map of the plasmid pUBGDH1 wherein UB is ubiquitin.

Figure 10:
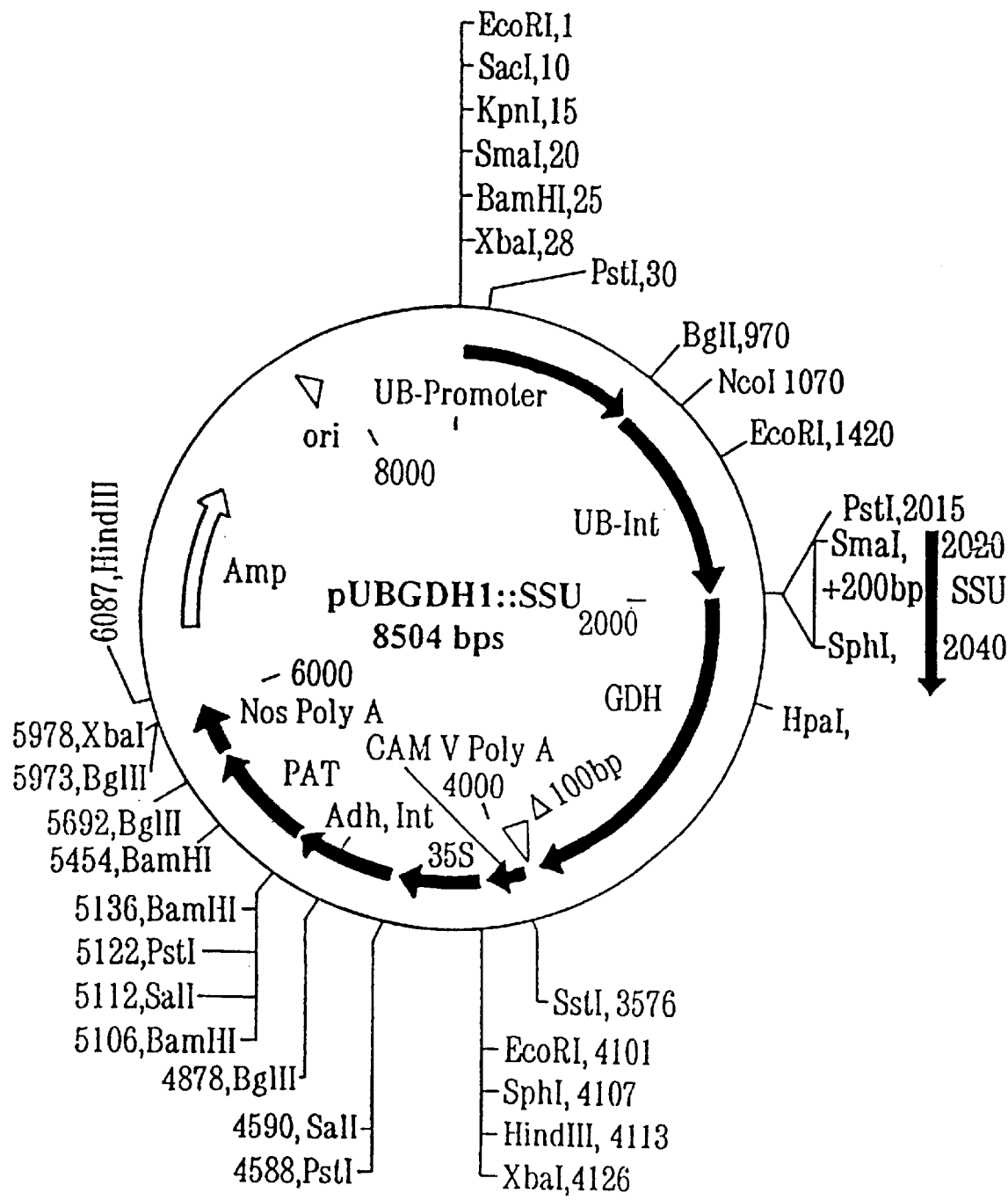

FIG. 10 shows a circular map of the plasmid vector PUBGDHI with the pre SS unit.

Figure 11:
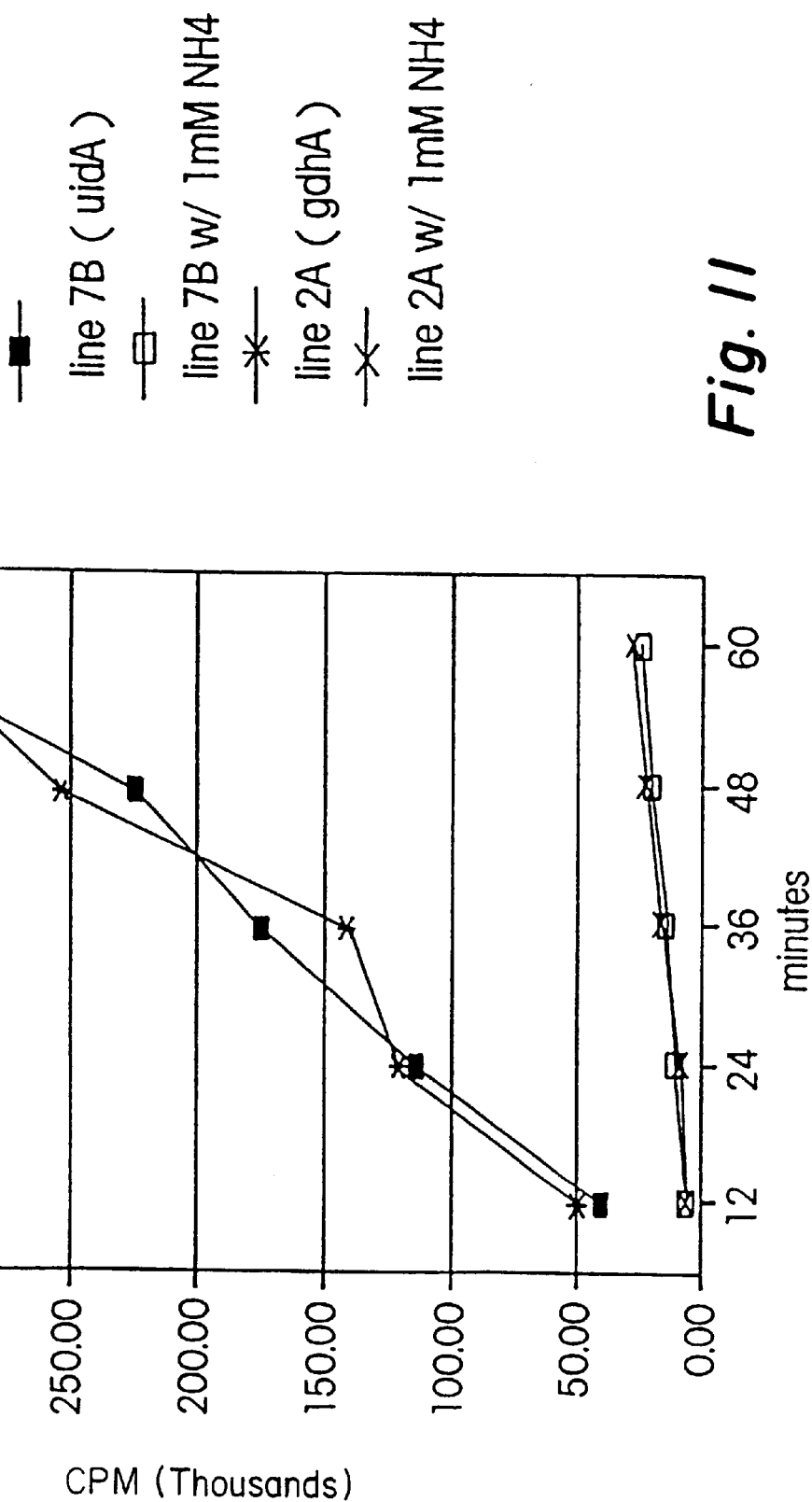

FIG. 11 shows the methylammonium uptake of tobacco transformants.

DETAILED DESCRIPTION OF THE INVENTION

The present invention relates to methods of producing transgenic plants containing the gdbA gene. The term transgenic plant refers to plants having exogenous genetic sequences which are introduced into the genome of a plant by a transformation method and the progeny thereof.

Transformation Methods—are means for integrating new genetic coding sequences by the incorporation of these sequences into a plant of new genetic sequences through man assistance.

Though there are a large number of known methods to transform plants, certain types of plants are more amenable to transformation than are others. Tobacco is a readily transformable plant. The basic steps of transforming plants are known in the art. These steps are concisely outlined in U.S. Pat. No. 5,484,956 "Fertile Transgenic Zea mays Plants Comprising Heterologous DNA Encoding Bacillus Thuringiensis Endotoxin" issued Jan. 16, 1996 and U.S. Pat. No. 5,489,520 "Process of Producing Fertile Zea mays Plants and Progeny Comprising a Gene Encoding Phosphinothricin Acetyl Transferase" issued Feb. 6, 1996.

1. Plant Lines

Plant cells such as maize can be transformed by a number of different techniques. Some of these techniques which have been reported on and are known in the art include maize pollen transformation (See University of Toledo 1993 U.S. Pat. No. 5,177,010); Biolistic gun technology (See U.S. Pat. No. 5,484,956); Whiskers technology (See U.S. Pat. Nos. 5,464,765 and 5,302,523); Electroporation; Agrobacterium (See 1996 article on transformation of maize cells in Nature Biotechnology, Volume 14, June 1996) along with numerous other methods which may have slightly lower efficiency rates then those listed. Some of these methods require specific types of cells and other methods can be practiced on any number of cell types.

The use of pollen, cotyledons, meristems and ovum as the target issue can eliminate the need for extensive tissue culture work. However, the present state of the technology does not provide very efficient use of this material.

Generally, cells derived from meristematic tissue are useful. Zygotic embryos can also be used. Additionally, the method of transformation of meristematic cells of cereal is also taught in the PCT application WO96/04392. Any of the various cell lines, tissues, plants and plant parts can and have been transformed by those having knowledge in the art. Methods of preparing callus from various plants are well known in the art and specific methods are detailed in patents and references used by those skilled in the art.

Cultures can be initiated from most of the above identified tissue. The material used herein was zygotic embryos. The embryos are harvested and then either transformed or placed in media. Osmotic cell treatments may be given to enhance particle penetration, cell survival, etc.

The only true requirement of the transformed material is that it can form a fertile transformed plant. This gene can be used to transform a number of plants both monocots and dicots. The plants that are produced as field crops are particularly useful. These crops can include cotton, corn, soybeans, wheat, sorghum, brassica, sunflower and some forage grasses and vegetables. The cereal grains appear to have the most economic advantage presently. The gdhA gene can come from various non-plant genes (such as; bacteria, yeast, animals, viruses). The gdhA gene can also come from plants. The gene insert used herein was either an E. coli glutamate dehydrogenase gene or a mutagenized version thereof. Another gdhA gene of particular interest is from Chlorella.

The DNA used for transformation of these plants clearly may be circular, linear, double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The gdhA gene can be useful to change or alter the nitrogen assimilation pathway or to assist in the identification and/or heartiness of transformed material in the presence of herbicide. Clearly, the bar gene from Streptoinycin hygroscopicus which encodes phosphinothricin acetyl transferase is resistance to phosphinothricin, and bialaphos herbicides (see U.S. Pat. No. 5,484,956, Table 1). Thus, this gene is useful as a selectable marker gene.

Surprisingly, the present gene is tolerant to some levels of phosphinothricin (including glufosinates) and bialaphos though in the constructs tested, the present gene may evidence slightly more susceptibility to herbicide damage at high herbicide concentration then plants transformed with the bar and PAT genes. However, when the gdhA gene is combined with the PAT and/or bar gene, the transformed cells and/or plants have increased regenerability and heartiness after herbicide selection, particularly to Ignite.

The regulatory promoters employed in the present invention can be constitutive such as CaMv35S for dicots and polyubiquitin for monocots or tissue specific promoters such as CAB promoters, etc. The prior art promoter include but is not limited to octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. Many dicots can easily be transformed with Agrobacterium. Some monocots are more difficult to transform. As previously noted, there are a number of useful transformation processes. The improvements in transformation technology are beginning to eliminate the need to regenerate plants from cells. Since 1986, the transformation of pollen has been published and recently the transformation of plant meristems have been published. The transformation of ovum, pollen, and seedlings meristem greatly reduce the difficulties associated with cell regeneration of different plants or genotypes within a plant can present.

The most common method of transformation is referred to as gunning or microprojectile bombardment. This biolistic process has small gold coated particles coated with DNA shot into the transformable material. Techniques for gunning DNA into cells, tissue, callus, embryos, and the like are well known in the prior art.

After the transformation of the plant material is complete, the next step is identifying the cells or material which has been transformed. In some cases, a screenable marker is employed such as the beta-glucuronidase gene of the uidA locus of E. coli. Thus, the cells expressing the colored protein are selected for either regeneration or further use. In many cases, the transformed material is identified by a selectable marker. The putatively transformed material is exposed to a toxic agent at varying concentrations. The cells which are not transformed with the selectable marker that provides resistance to this toxic agent die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. The present invention is useful as a selectable marker for identifying transformed materials in the presence of the herbicide phosphinothricin. In fact, when combined with the PAT or bar gene which is known to give resistance to phosphinothricin, the cells or plants after exposure to the herbicide often evidences increased growth by weight and appear more vigorous and healthy.

If the transformed material was cell lines then these lines are regenerated into plants. The cell's lines are treated to induce tissue differentiation. Methods of regeneration of cellular material are well known in the art since early 1982. The plants from either the transformation process or the regeneration process are transgenic plants.

The following non-limiting examples are shown to more particularly describe the present invention.

The DNA sequence of the gdhA gene of *Escherichia coli* which encodes a 447 amino acid polypeptide subunit of NADP-specific glutamate dehydrogenase was presented in 1982 in Nucleic Acids Research, Volume II, Number 15, 1983. The present examples will illustrate the gdhA gene transformed into both dicot and monocot plants.

EXAMPLE I

Fertile transgenic tobacco plants containing an isolated gdhA gene was prepared as follows:

A. The Tobacco Tissue for Transformation was Initiated and Maintained.

Seed from *Nicotiana tabacum* var. Petite Havana were surface sterilized and germinated on MSO medium (Murashige and Skoog 1962). Two weeks after germination, leaves were excised and used in transformation experiments.

B. Formation of the Plasmid.

A bacterial glutamate dehydrogenase (gdhA) gene, shown in FIG. 1 (SEQ ID NO:1), derived from *E. coli*, was altered for expression in plant cells by polymerase chain reaction. The 5' non-coding region was modified by the introduction of an XbaI restriction enzyme site. Kozac's consensus sequence (Lutcke et. al. 1987) was also added to the 5' region (SEQ ID NOS:5–7) to allow high levels of expression in plant cells. The 3' non-coding region (SEQ ID NOS:8–10) was altered to stabilize the mRNA and ensure appropriate polyadenylation and a SacI restriction site was added. These primer sequences, shown in FIG. 2 (SEQ ID NOS:3–4), are the introduction of the restriction sites and the Kozac's consensus sequence along with the destabilizing portions. The amino acid sequence of the gdhA gene was retained. PCR was carried out in an automated thermal cycler (MJ Research, St. Louis, Mo.) for 25 cycles (each cycle consisting of 1 min. at 92° C., 1 min. at 60° C. and 3 min. at 72° C). Reactions contained 200 ng of pBG1 (Mattaj et. al. 1981), 0.9 mM) $MgCL_2$, dNTPs, 1 unit of Taq polymerase (Promega, Madison, Wis.) and 1 nM of each primer. The PCR products were gel purified and DNA bands recovered from agarose gels using GeneClean (Bio101, Hercules, Calif.). XbaI and SacI were used with the band which was digested. This process provided single strand complementary end for ligation into a vector.

The uidA gene from pBI121.1 (pBI121 plasmid is commercially available from Clontech Laboratories, Palo Alto, Calif.), (Jefferson, 1987) was removed by restriction digest with XbaI and SacI and the gel eluted PCR products were ligated into the resulting 9.7 kb fragment of pBI121.1. The amino acid sequence of the GDH enzyme produced by the gdhA gene is shown in (SEQ ID NO:11) FIG. 3. The plasmids were then transformed into competent *E. coli* cells (Top10 Invitrogen, San Diego, Calif.) via electroporation. Colony hybridization was used to detect colonies with the modified gdhA inserts (FIG. 3). Plasmids from the hybridizing colonies were used to transform competent Agrobacterium tumefaciens (Sambrook et. al. 1989) strains LBA4404 (Hooykas 1981) and EHA101 (Nester 1984).

C. Plant Transformation.

*Nicotiana tabacum* var. Petite Havana leaf discs from in vitro grown seedlings were transformed with the A. tumefaciens constructs using standard tobacco transformation procedures (Horsch et. al. 1988) with the following modification. Transformed shoots were selected on 300 μg/ml kanamycin. Shoots were excised and rooted in a sterile peat-based medium in GA7 vessels (Magenta Corp. Chicago, Ill.). The vessel lids were gradually removed (over 7–10 days) to acclimatize the plantlets to laboratory conditions before placement in the greenhouse.

D. Confirmation of Transformation with gdhA Gene.

To show that the tobacco has acquired the gdhA gene the specific activity of GDH was quantified by measuring the rate of oxidation of NADPH due to 2-oxoglutamate reductive amination. This enzyme assay was performed on cell free extracts.

1. Cell Free Extract Preparation

Leaf tissue (1–2 g) was placed in 5 volumes of ice-cold buffer(200 mM Tris-HCL pH8.0, 14 mM).

2. Mercaptoethanol, 10 mM L-cysteine, 0.5 mM phenylmethylsulphonylfluroide, 0.5% (v/v) Triton x-100) [23]. Tissue was homogenized by Polytron (Tekmar, Cincinnati, Ohio) 4 times for 12 seconds each and was returned to an ice bath for 12 seconds between each grind. The slurry was centrifuged at 10,000 g for 25 minutes and the supernatant was used for enzyme assays. *E. coli* extracts were prepared as in Mountain et. al., 1985 [32]. This publication is hereby incorporated by reference. All steps were carried out at 4° C.

Gel Analysis and GDH Activity Staining

Regenerants were qualitatively tested for deaminating NADP-dependent GDH activity following gel electrophoresis of crude protein extracts after Lightfoot et. al., 1988. Electrophoresis of other protein extracts is known to those skilled in the art. Proteins were separated on a non-denaturing gel containing 5% polyacrylamide by electrophoresis for 2 hr at 120 V. NADP-specific GDH enzyme activity was visualized as a band in the gel by L-glutamate and NADP-dependent tetrazolium staining of GDH isozymes (50 mM Tris pH 9.3, 8 mg/ml glutamate, 0.04 mg/ml NADP, 0.04 mg/ml MTT, 0.04 mg/ml phenazine monosulphate and 0.08 mg/ml $CaCl_2$).

Enzyme assays

The specific activity of aminating NADPH-dependent GDH in cell free extracts was quantified by measuring the rate of oxidation of NADPH attributable to the reductive amination of 2-oxoglutarate. The reaction mixture initially consisted of 0.1 M Tris pH 8.5, 0.2M 2-α-ketoglutarate, 1.0 MM $CaCl_2$, 0.2 mM NADPH, 200 mM ammonium chloride and 50 mM glutamine. The rate of change in absorption was measured at 340 nm for 1.5 minutes before and 1.5 minutes after the addition of the 20 mM or 200 mM ammonium chloride. Glutamine was then added to 5 mM and the absorbance measured for a further 1.5 minutes. Assays were performed at 25° C.

Glutamine synthetase activity was measured spectrophotometrically by incubating the crude extract in a reaction mixture for 10 minutes by the transferase assay as taught in the art (see Cullinore J. V. *Planta* 150.39 2–396, 1980). The $OD_{500}$ was measured, 1 μM γ-glutamyl hydroxamate has an $OD_{500}$ of 0.4.

Glutamate concentration determination

Glutamate and glutamine concentrations were determined after separation on Dowex-1-acetate. Quantitation was by the ninhydrin spectrophotometric assay.

TABLE 1

Characteristics of Transgenic Plants

| | | Number of Lines | |
|---|---|---|---|
| Strain/Gene | Explants Inoculated | Antibiotic Resistant[a] | GDH[+b] |
| EHA101/gdhA | 30 | 17 | 12 |
| LBA4404/gdhA | 30 | 2 | 2 |

[a] = Resistant to 300 μg/ml kanamycin in an $R_1$ seedling assay.
[b] = Positive bands after electrophoresis of crude extract on 5% polyacrylamide gel followed by NADP-dependent tetrazolium staining of GDH isozymes.

EXAMPLE II

The original plant transformation vector pBI121.1 was modified in Example I to contain the gdhA gene. In this example, the vector was unchanged and pBI121.1 containing uidA was used as the chimeric plasmid which was transformed into *E. coli* cells (Top10 Invitrogen, San Diego, Calif.) via electroporation. Colony hybridization was used to detect colonies with plasmids containing uidA gene. Plasmids from the hybridizing colonies were analyzed by single and double restriction digestions. Plasmids with the correct physical map were used to transform competent *Agrobacterium tumefaciens* strains LBA4404 and EHA101.

Plant Transformation.

*Nicotiana tabacum* var. Petite Havana leaf discs from in vitro grown seedlings were transformed with the *A. tumefaciens* constructs using standard tobacco transformation procedures as in the earlier example with the following modification. Transformed shoots were selected on 300 μg/ml kanamycin. Shoots were excised and rooted in a sterile peat-based medium in GA7 vessels (Magenta Corp. Chicago, Ill.). The vessel lids were gradually removed (over 7–10 days) to acclimatize the plantlets to laboratory conditions before placement in the greenhouse. The $R_0$ plants were allowed to flower and self fertilize to produce the $R_1$ seed. $R_1$ seed were collected from individual plants and stored at 4° C.

TABLE 2

Characteristics of uidA

| | | Number of Lines | |
|---|---|---|---|
| Strain/Gene | Explants Inoculated | Antibiotic Resistant[a] | GDH[+b] |
| LBA4404/uidA | 15 | 2 | 0 |
| EHA101/uidA | 15 | 4 | 0 |

[a] = Resistant to 300 μg/ml kanamycin in an $R_1$ seedling assay.
[b] = Positive bands after electrophoresis of crude extract on 5% polyacrylamide gel followed by NADP-dependent tetrazolium staining of GDH isozymes.

Discussion of Examples I and II.

A non denaturing polyacrylamide gel containing bands produced from NADP-dependent staining of crude extracts of *E. coli*, gdhA transformed lines and one uidA line was performed and read. As expected, the uidA transformed line did not produce bands when stained with $NADP^+$ as the oxidant. Fourteen of the 19 antibiotic resistant gdhA transformants showed GDH activity as did the *E. coli*.

TABLE 3

Specific activity of NADPH-dependent GDH and ATP dependent GS in cell-free extracts of transgenic tobacco

| Tobacco Line | Transforming Gene | GDH Activity NADPH Oxidation nM/mg[a]/min | GS activity nM/mg/min |
|---|---|---|---|
| 2A | gdhA | 2046 | 38 |
| $8_2$ | gdhA | 1600 | 71 |
| $9_1$ | gdhA | 1063 | 85 |
| 7B | uidA | 0 | 85 |
| *E. coli* | gdhA | 215 | 59 |

[a] = Specific activity per mg of soluble protein.

Enzyme Specific Activity of Examples I and II.

High specific activities of GDH in gdhA transformed $R_0$ tobacco leaves were observed. The gdhA transformed tobacco lines produced up to 10 times more activity than gdhA in *E. coli*. NADP-specific GDH activity was not detectable in the uidA transformed tobacco lines.

GS activity was somewhat reduced in leaves of plant lines where the GDH activity was more than about 1100 nM/mg protein/min. The GDH activity was about 15–50 fold greater than the GS activity in the cell free extracts with saturating substrate concentrations. The GDH activity was not greatly reduced in assays containing 20 mM ammonium (data not shown) close to physiological $NH_4$ concentrations. Therefore, gdhA transformed plants may be assimilating ammonium at a rate equivalent to, or better than, GS.

The specific activity of GDH in cell free extracts show gdhA gene in plants at 5–10 times the *E. coli* gdhA activity. This was surprising as there was initially some question as to whether the bacterial gene would express well in the plant genome. The gdhA gene in plants have a GDH activity that is 15–50 times greater than the GS activity. Increased ammonium assimilation is apparently provided by GDH activity if substrate concentrations are not limiting.

Ammonium assimilation by GDH is energetically favorable compared to GS since there is a net saving of one ATP. In addition, the higher specific activity of GDH might require the synthesis of 10 fold fewer enzyme molecules per mole of ammonium assimilated.

EXAMPLE III

Fertile transgenic tobacco containing gdhA gene and chloroplast transit peptides:

The plasmid constructed in Example I (shown in FIG. 4) does not target the gdhA gene to the area of tissue that it is presumed to be most helpful. The chloroplasts of the plant tissue is targeting in the present example. The pBI121 gdhA plasmid was modified to allow fusion with cleavable preprotein sequences (often referred to as chloroplast transit peptide sequences) from RUBISCO SSU (rbcS) by introduction of the SphI site. PCR amplification of gdhA from pBI121::GDH1 using the mutagenic primer.

Primer SPHGDH5 (SEQ ID NO:17)

GGT TTT ATA TgC ATg CAT CAg ACA TAT TC 5' SphI adapter for ligation of gdhA with chloroplast targeting pre-peptide encoding sequences.

And the addition of the specific primer HUGDH3 (shown in FIG. 6B) was completed. The amplified 1.3 kbp fragment was subject to restriction digestion with SphI and SacI. Digestion of pBI121 with SmaI and SacI allowed recovery of the vector minus GUS (uidA) as a 9.6 kbp fragment. PCR amplification from the plasmid pPSR6 (Cashmore et. al., 1983) and restriction digestion allowed recovery of the preprotein encoding sequence as a 0.2 kbp fragment SmaI to SphI fragment. The 9.6 kbp pBI121 fragment was ligated with the 1.3 kbp fragment from pBI121::GDH1 and the 0.2 kbp fragment from pPRS6 to give pBI121::SSU::GDH1 (shown in FIG. 7) which was amplified in *E. coli* DH5.

Results of Examples

The transformed tobacco plants, leaves and seed Examples I and II were analyzed for percentage of nitrogen, protein and crude fat with the following result:

TABLE 4

| Tobacco Leaf Analysis | | |
|---|---|---|
| | % N | % Protein |
| uidA transformed | 6.98 | 43.6 |
| gdhA transformed | 8.01 | 50.0 |

| Tobacco Seed Analysis | | | |
|---|---|---|---|
| | % N | % Protein | Crude Fat |
| uidA transformed | 4.2 | 26.5 | 36.9 |
| gdhA transformed | 3.56 | 22.0 | 35.07 |
| nontransformed | 3.98 | 25.0 | 38.5 |

The leaf analysis shows a 1% nitrogen increase and a 6% increase in protein in the gdbA transformed plant. The seed analysis appears to indicate that the gdhA gene may be altering the accumulation of nitrogen, protein and crude fat in the tobacco seed.

EXAMPLE IV

Ammonium Toxicity

The transformed tobacco seeds of the previous examples were used in an ammonium toxicity study. Ammonium toxicity was measured by germinating transformed tobacco seed on agar solidified MS media while excluding all nitrogen sources except ammonium chloride. The medium was supplemented with 10, 30, 50, 70 or 100 mM ammonium chloride but no nitrates. The seedlings were grown either with or without 30 mg/1 sucrose. Ten to fifteen $R_1$ seeds were initiated per plate with four replications per concentration. Fresh and dry weights of 10 seedlings per plate were measured after six weeks on these media. Table 5 shows these results.

TABLE 5

Effect of concentration of ammonium chloride and genotype on dry weight of gdhA or uidA transformed $R_1$ tobacco seedlings. No carbon source supplied.

| | Dry weight (mg) of Transformed Lines | | | | | | | | | |
|---|---|---|---|---|---|---|---|---|---|---|
| | 2A | | $8_2$ | | $9_1$ | | 7B | | | $LSD^c$ values |
| NH4 Conc. | (gdhA) | $n^a$ | (gdhA) | n | (gdhA) | n | (uidA) | n | Significance[b] | 5% | 1% |
| 10 nM | 0.75 | 40 | 1.3 | 29 | 0.48 | 39 | 0.85 | 20 | ** | 0.25 | 0.33 |
| 30 | 1.2 | 34 | 0.8 | 36 | 0.57 | 36 | 0.6 | 39 | ** | 0.31 | 0.40 |
| 50 | 0.6 | 30 | 0.36 | 39 | 0.38 | 28 | 0.4 | 38 | ** | 0.14 | 0.19 |
| 70 | 0.36 | 39 | 0.35 | 40 | 0.21 | 40 | 0.25 | 38 | ** | 0.08 | 0.11 |
| 100 | 0.19 | 36 | 0.18 | 29 | 0.14 | 40 | 0.17 | 40 | ** | 0.06 | 0.07 |
| Significance | ** | | ** | | ** | | ** | | | | |

TABLE 5-continued

Effect of concentration of ammonium chloride and genotype on dry weight of gdhA or uidA transformed $R_1$ tobacco seedlings. No carbon source supplied.

| | Dry weight (mg) of Transformed Lines | | | | | | | | | |
|---|---|---|---|---|---|---|---|---|---|---|
| | 2A | | $8_2$ | | $9_1$ | | 7B | | | LSD[c] values | |
| NH4 Conc. | (gdhA) | n[a] | (gdhA) | n | (gdhA) | n | (uidA) | n | Significance[b] | 5% | 1% |
| LSD value | | | | | | | | | | | |
| 5% | 0.28 | | 0.21 | | 0.10 | | 0.10 | | | | |
| 1% | 0.36 | | 0.28 | | 0.13 | | 0.14 | | | | |

[a]n = number of seedlings
[b]** = significant results at the 1% level, NS = nonsignificant
[c]LSD = Lease Significant Difference as calculated by $T_{df}(MSE/n)^{1/2}$ Increased resistance to ammonium chloride is partial as the GDH activity would affect primarily the nitrogen assimilation rate. Increased resistance to ammonium chloride is evident by the increase in fresh and dry weight accumulated by the gdba transformed lines.

EXAMPLE V
Field Traits of Transgenic Tobacco

The transformed tobacco was planted in a field and fertilized with 150 lb. per acre of ammonium nitrate. The following data on the field traits was collected.

If the control is the uidA gene in the transformed tobacco plants then the significant differences are in the leaf number and the leaf length between the 91 line and the 7B line. The Bar data across the chart, with the sole exception of the nitrogen content, is lower then the 7B line. It is within the LSD. If Bar is used as the control, dry weight and plant height (yield) is also significantly greater for Line 91. Clearly, increasing leaf number and leaf length is of increased value when that portion of the plant is part of what is harvested. For example, this increased biomass is important in silage, and forage grasses such as alfalfa, clover and the like.

TABLE 6A (150# per Acre of Nitrogen)
gdhA transformed *Nicotina tabaccum* variety 'Petite Havana' lines 913 & 2A1, uidA transformed line 7B1 and bar transformed line BAR were grown under field conditions in a completely randomized block design. Data were collected after 12 weeks on height, # of leaves and length and width of the most recent fully expanded leaf. Plants were harvested at ground level and dried for 3 days to determine dry weight (DWT.).

| Line | DWT | n | Height[a] | n | # of Leaves[b] | n | Length[c] | n | Width[d] | n[e] |
|---|---|---|---|---|---|---|---|---|---|---|
| 2A1 | 23.78 | 5 | 37.3456 | 90 | 17.167 | 90 | 23.1689 | 90 | 11.786 | 90 |
| 913 | 28.74 | 5 | 41.2224 | 85 | 13.765 | 85 | 24.9012 | 85 | 13.415 | 85 |
| 7B1 | 19.18 | 5 | 41.4822 | 90 | 13.556 | 90 | 24.1311 | 90 | 13.21 | 90 |
| Bar | 10.3 | 5 | 36.16 | 82 | 13.585 | 82 | 22.5159 | 82 | 13.794 | 82 |
| Sig.[f] | 0.0393 | | 0.0001 | | 0.0001 | | 0.0001 | | 0.2477 | |
| LSD.05 | 12.34 | | 1.597 | | 2.17 | | 1.147 | | 2.198 | |

[a]height was measured to the top of the most recent fully expanded leaf
[b]the number of leaves greater than 10 cm
[c]the length of the most recent fully expanded leaf was measured
[d]the width of the most recent fully expanded leaf was measured
[e]n = number of replications

TABLE 6B (150# per Acre of Nitrogen)
Means Analysis
gdhA transformed *Nicotina tabaccum* variety 'Petite Havana' lines 913 & 2A1, uidA transformed line 7B1 and bar transformed line BAR were grown under field conditions in a completely randomized block design. Data were collected after 12 weeks on height, # of leaves and length and width of the most recent fully expanded leaf. Plants were harvested at ground level and dried for 3 days to determine dry weight (DWT.).

| Line | DWT | n | Height[a] | n | # of Leaves[b] | n | Length[c] | n | Width[d] | n[e] |
|---|---|---|---|---|---|---|---|---|---|---|
| 2A1 | 209.8 | 6 | 56.7 | 6 | 58.1 | 6 | 30.8 | 6 | 17.5 | 6 |
| 913 | 223.1 | 6 | 55 | 6 | 61.8 | 6 | 31.8 | 6 | 18.2 | 6 |

TABLE 6B-continued (150# per Acre of Nitrogen)
Means Analysis
gdhA transformed *Nicotina tabaccum* variety 'Petite Havana' lines 913 & 2A1,
uidA transformed line 7B1 and bar transformed line BAR were grown under field conditions
in a completely randomized block design. Data were collected after 12 weeks on height,
of leaves and length and width of the most recent fully expanded leaf.
Plants were harvested at ground level and dried for 3 days to determine dry weight (DWT.).

| Line | DWT | n | Height[a] | n | # of Leaves[b] | n | Length[c] | n | Width[d] | n[e] |
|---|---|---|---|---|---|---|---|---|---|---|
| 7B1 | 204.3 | 6 | 57.9 | 6 | 39.3 | 6 | 27 | 6 | 14.7 | 6 |
| Bar | 203.4 | 6 | 59.2 | 6 | 48.4 | 6 | 29.4 | 6 | 16.8 | 6 |
| Sig.[f] | 0.589 | | 0.3498 | | 0.0145 | | 0.0087 | | 0.0072 | |
| LSD$_{.05}$ | | | | | 13.9 | | 2.64 | | 1.9 | |

[a] height was measured to the top of the most recent fully expanded leaf
[b] the number of leaves greater than 10 cm
[c] the length of the most recent fully expanded leaf was measured
[d] the width of the most recent fully expanded leaf was measured
[e] n = number of replications

TABLE 6C (75# per Acre of Nitrogen)
Means Analysis
gdhA transformed *Nicotina tabaccum* variety 'Petite Havana' lines 913, 2A1,
uidA transformed line 7B1 and bar transformed line BAR were grown under field conditions
in a completely randomized block design. Data were collected after 12 weeks on height,
of leaves and length and width of the most recent fully expanded leaf.
Plants were harvested at ground level and dried for 3 days to determine dry weight (DWT.).

| Line | DWT | n | Height[a] | n | # of Leaves[b] | n | Length[c] | n | Width[d] | n[e] |
|---|---|---|---|---|---|---|---|---|---|---|
| 2A1 | 190.9 | 6 | 57.2 | 6 | 46.8 | 6 | 29.1 | 6 | 16.4 | 6 |
| 913 | 189.9 | 6 | 56.8 | 6 | 49.3 | 6 | 28.8 | 6 | 16.4 | 6 |
| 7B1 | 165.6 | 6 | 57.2 | 6 | 26.2 | 6 | 24.6 | 6 | 13.3 | 6 |
| Bar | 185.5 | 6 | 54 | 6 | 44.8 | 6 | 27.7 | 6 | 15.7 | 6 |
| Sig.[f] | 0.058 | | 0.3261 | | 0.0048 | | 0.0024 | | 0.0007 | |
| LSD$_{.05}$ | 20.17 | | | | 12.38 | | 2.2 | | 1.39 | |

[a] height was measured to the top of the most recent fully expanded leaf
[b] the number of leaves greater than 10 cm
[c] the length of the most recent fully expanded leaf was measured
[d] the width of the most recent fully expanded leaf was measured
[e] n = number of replications

TABLE 6D

Combined Data
(150# per Acre of Nitrogen)
gdhA transformed *Nicotiana tabaccum* variety 'Petite Havana' (GDH+) and GDH– Nicotiana
were grown under field conditions in a completely randomized block design. Data were collected
after 12 weeks on height, # of leaves and length and width of the most recent fully expanded leaf.
Plants were harvested at ground level and dried for 3 days to determine dry weight (DWT.).

| Line | Dry Weight | n | Height[a] | n | # of Leaves[b] | n | Length[c] | n | Width[d] | n[e] |
|---|---|---|---|---|---|---|---|---|---|---|
| GDH+ | 130.01 | 22 | 41.3 | 494 | 20.15 | 494 | 24.7 | 494 | 13.13 | 494 |
| GDH– | 117.87 | 22 | 41.16 | 450 | 16.8 | 450 | 23.8 | 450 | 13.69 | 450 |
| Sig.[f] | 0.6944 | | 0.9467 | | 0.012 | | 0.0091 | | 0.4054 | |
| LSD$_{.05}$ | | | | | 2.614 | | 0.6957 | | 1.339 | |

[a] height was measured to the top of the most recent fully expanded leaf
[b] the number of leaves greater than 10 cm
[c] the length of the most recent fully expanded leaf was measured
[d] the width of the most recent fully expanded leaf was measured In another experiment the same Tobacco lines were grown at two application rates of N, 75 lb. per acre and 150 lb. per acre. The N applied was in the form of anhydrous ammonia rather than the ammonium nitrate used in the previous experiment. Results showed a consistent numerical advantage, though not statistically different advantage, to gdhA transformed plant lines over uidA or bar transformed plant lines in dry weight, number of leaves and width of leaves at both 175 and 150 lb. of applied nitrogen (Table 6B and Table 6C).

Combined results for both experiments showed a consistent numerical advantage to gdhA transformed plant lines over uidA and bar transformed plant lines in dry weight and number of leaves (Table 6D). However, the differences were not statistically different since the data contained a lot of variability caused by weed pressure on the peripheral plots.

TABLE 6G

Amino Acid Analysis
150# per Acre
Amino acid analyses of seed samples collected from field grown gdhA transformed tobacco lines 2A1, 913, 842 and 9Z1, uidA transformed tobacco line 7B1 and bar transformed tobacco line BAR. These numbers represent the proportion of the total hydrolyzable amino acids.

|  | GDH+ | GDH− | P value | LSD$_{.05}$ |
|---|---|---|---|---|
| ALANINE | 0.0518 | 0.0503 | 0.0003 | 0.0007775 |
| ARGININE | 0.1123 | 0.1155 | 0.0081 | 0.0022710 |
| ASPARTIC ACID | 0.1194 | 0.1159 | 0.0116 | 0.0026200 |
| GLUTAMIC ACID | 0.2057 | 0.2111 | 0.0001 | 0.0021230 |
| GLYCINE | 0.0539 | 0.0534 | 0.0553 | 0.0004969 |
| HISTIDINE | 0.0227 | 0.0225 | 0.2521 | 0.0036150 |

TABLE 6E

Amino Acid Analysis
150# per Acre
Amino acid analyses of seed samples collected from field grown gdhA transformed tobacco lines 2A1, 913, 842, and 9Z1 uidA transformed tobacco line 7B1 and bar transformed tobacco line BAR. These numbers represent the proportion of the total hydrolyzable amino acids.

|  | 2A1 | #913 | #842 | 9Z1 | 7B1 | BAR | P value | LSD$_{.05}$ |
|---|---|---|---|---|---|---|---|---|
| ALANINE | 0.0525 | 0.0519 | 0.0513 | 0.0518 | 0.0504 | 0.0501 | 0.0110 | 0.0013 |
| ARGININE | 0.1095 | 0.1116 | 0.1146 | 0.1133 | 0.1157 | 0.1153 | 0.0046 | 0.0033 |
| ASPARTIC ACID | 0.1225 | 0.1210 | 0.1170 | 0.1174 | 0.1153 | 0.1165 | 0.0027 | 0.0036 |
| GLUTAMIC ACID | 0.2036 | 0.2058 | 0.2065 | 0.2071 | 0.2105 | 0.2116 | 0.0004 | 0.0033 |
| GLYCINE | 0.0544 | 0.0533 | 0.0541 | 0.0537 | 0.0537 | 0.0532 | 0.0128 | 0.0007 |
| HISTIDINE | 0.0227 | 0.0227 | 0.0226 | 0.0227 | 0.0222 | 0.0227 | 0.4617 | 0.0006 |
| ISOLEUCINE | 0.0425 | 0.0434 | 0.0414 | 0.0441 | 0.0422 | 0.0442 | 0.1552 | 0.0025 |
| LEUCINE | 0.0725 | 0.0731 | 0.0730 | 0.0733 | 0.0732 | 0.0731 | 0.4910 | 0.0010 |
| LYSINE | 0.0322 | 0.0331 | 0.0309 | 0.0326 | 0.0310 | 0.0320 | 0.0006 | 0.0010 |
| METHIONINE | 0.0069 | 0.0071 | 0.0096 | 0.0092 | 0.0084 | 0.0067 | 0.1719 | 0.0029 |
| PHENYLALANINE | 0.0504 | 0.0508 | 0.0500 | 0.0515 | 0.0506 | 0.0508 | 0.0035 | 0.0063 |
| PROLINE | 0.0521 | 0.0483 | 0.0502 | 0.0486 | 0.0504 | 0.0488 | 0.0423 | 0.0026 |
| SERINE | 0.0490 | 0.0487 | 0.0498 | 0.0472 | 0.0496 | 0.0407 | 0.3473 | 0.0095 |
| THREONINE | 0.0456 | 0.0451 | 0.0453 | 0.0442 | 0.0445 | 0.0440 | 0.0106 | 0.0010 |
| TYROSINE | 0.0317 | 0.0304 | 0.0332 | 0.0289 | 0.0309 | 0.0286 | 0.0331 | 0.0030 |
| VALINE | 0.0521 | 0.0535 | 0.0505 | 0.0544 | 0.0511 | 0.0547 | 0.0668 | 0.0034 |

TABLE 6F

Amino Acid Analysis
75# per Acre
Amino acid analyses of seed samples collected from field grown gdhA transformed tobacco lines 2A1, 913, 842, and 9Z1, uidA transformed tobacco line 7B1 and bar transformed tobacco line BAR. These numbers represent the proportion of the total hydrolysable amino acids.

|  | 2A1 | #913 | #842 | 9Z1 | 7B1 | BAR | P value | LSD$_{.05}$ |
|---|---|---|---|---|---|---|---|---|
| ALANINE | 0.0526 | 0.0521 | 0.0520 | 0.0518 | 0.0501 | 0.0501 | 0.0326 | 0.0013 |
| ARGININE | 0.1110 | 0.1160 | 0.1170 | 0.1159 | 0.1186 | 0.1003 | 0.5925 | 0.0232 |
| ASPARTIC ACID | 0.1168 | 0.1117 | 0.1111 | 0.1112 | 0.1111 | 0.1110 | 0.0032 | 0.0032 |
| GLUTAMIC ACID | 0.2016 | 0.2039 | 0.2037 | 0.2070 | 0.2076 | 0.2104 | 0.0001 | 0.0031 |
| GLYCINE | 0.0544 | 0.0550 | 0.0549 | 0.0542 | 0.0545 | 0.0538 | 0.0391 | 0.0079 |
| HISTIDINE | 0.0237 | 0.0228 | 0.0228 | 0.0230 | 0.0230 | 0.0230 | 0.4914 | 0.0010 |
| ISOLEUCINE | 0.0430 | 0.0407 | 0.0427 | 0.0437 | 0.0427 | 0.0447 | 0.2471 | 0.0031 |
| LEUCINE | 0.0731 | 0.0733 | 0.0745 | 0.0744 | 0.0737 | 0.0741 | 0.0233 | 0.0010 |
| LYSINE | 0.0348 | 0.0312 | 0.0311 | 0.0328 | 0.0305 | 0.0320 | 0.0062 | 0.0022 |
| METHIONINE | 0.0090 | 0.0104 | 0.0091 | 0.0079 | 0.0083 | 0.0069 | 0.1216 | 0.0025 |
| PHENYLALANINE | 0.0500 | 0.0511 | 0.0521 | 0.0520 | 0.0511 | 0.0513 | 0.1045 | 0.0014 |
| PROLINE | 0.0520 | 0.0508 | 0.0487 | 0.0480 | 0.0500 | 0.0469 | 0.0010 | 0.0022 |
| SERINE | 0.0494 | 0.0506 | 0.0501 | 0.0490 | 0.0496 | 0.0482 | 0.3649 | 0.0023 |
| THREONINE | 0.0454 | 0.0456 | 0.0455 | 0.0448 | 0.0452 | 0.0443 | 0.1248 | 0.0011 |
| TYROSINE | 0.0315 | 0.0346 | 0.0340 | 0.0306 | 0.0324 | 0.0294 | 0.0973 | 0.0040 |
| VALINE | 0.0518 | 0.0501 | 0.0518 | 0.0537 | 0.0520 | 0.0552 | 0.1631 | 0.0039 |

TABLE 6G-continued

Amino Acid Analysis
150# per Acre
Amino acid analyses of seed samples collected from field grown gdhA transformed tobacco lines 2A1, 913, 842 and 9Z1, uidA transformed tobacco line 7B1 and bar transformed tobacco line BAR. These numbers represent the proportion of the total hydrolyzable amino acids.

|  | GDH+ | GDH− | P value | LSD$_{.05}$ |
|---|---|---|---|---|
| ISOLEUCINE | 0.0428 | 0.0433 | 0.5632 | 0.0016700 |
| LEUCINE | 0.0730 | 0.0731 | 0.5401 | 0.0005836 |
| LYSINE | 0.0322 | 0.0315 | 0.1261 | 0.0008533 |
| METHIONINE | 0.0083 | 0.0077 | 0.5448 | 0.0018960 |
| PHENYLALANINE | 0.0507 | 0.0577 | 0.9641 | 0.0005084 |
| PROLINE | 0.0499 | 0.0495 | 0.6996 | 0.0018320 |
| SERINE | 0.0487 | 0.0477 | 0.1771 | 0.0057800 |
| THREONINE | 0.0450 | 0.0443 | 0.0254 | 0.0006688 |
| TYROSINE | 0.0310 | 0.0296 | 0.1691 | 0.0021120 |
| VALINE | 0.0526 | 0.0531 | 0.6792 | 0.0023360 |

TABLE 6H

Amino Acid Analysis
75# per Acre
Amino acid analyses of seed samples collected from field grown gdhA transformed tobacco lines 2A1, 913, 842 and 9Z1, uidA transformed tobacco line 7B1 and bar transformed tobacco line BAR. These numbers represent the proportion of the total hydrolyzable amino acids.

|  | GDH+ | GDH− | P value | LSD$_{.05}$ |
|---|---|---|---|---|
| ALANINE | 0.0522 | 0.0507 | 0.0009 | 0.0007800 |
| ARGININE | 0.1149 | 0.1086 | 0.3601 | 0.0138600 |
| ASPARTIC ACID | 0.1126 | 0.1108 | 0.1416 | 0.0024850 |
| GLUTAMIC ACID | 0.2041 | 0.2091 | 0.0001 | 0.0023290 |
| GLYCINE | 0.0546 | 0.0541 | 0.0663 | 0.0005187 |
| HISTIDINE | 0.0231 | 0.0230 | 0.7629 | 0.0006349 |
| ISOLEUCINE | 0.0426 | 0.0438 | 0.2308 | 0.0019700 |
| LEUCINE | 0.0739 | 0.0739 | 0.8276 | 0.0071220 |
| LYSINE | 0.0325 | 0.0313 | 0.1349 | 0.0016580 |
| METHIONINE | 0.0090 | 0.0075 | 0.0523 | 0.0015320 |
| PHENYLALANINE | 0.0511 | 0.0512 | 0.7059 | 0.0009534 |
| PROLINE | 0.0498 | 0.0481 | 0.0718 | 0.0018760 |
| SERINE | 0.0498 | 0.0488 | 0.1720 | 0.0014260 |
| THREONINE | 0.0453 | 0.0447 | 0.0652 | 0.0006861 |
| TYROSINE | 0.0326 | 0.0308 | 0.1647 | 0.0026340 |
| VALINE | 0.0519 | 0.0537 | 0.1463 | 0.0024610 |

TABLE 6I

Amino Acid Analysis
Corn
Amino acid analyses of grain samples collected from field grown transformed corn inbred lines H99 (untransformed), LL3-68 and These number represent the proportion of total hydrolyzable amino acids.

|  | H99 GDH− | LL3-68 GDH+ | LL8-67 GDH+ |
|---|---|---|---|
| Aspartic acid | 0.0614 | 0.0635 | 0.065300 |
| Threonine | 0.0371 | 0.0381 | 0.038400 |
| Serine | 0.0527 | 0.0531 | 0.053600 |
| Glutamic Acid | 0.2158 | 0.2092 | 0.217800 |
| Proline | 0.1061 | 0.0980 | 0.108800 |
| Glycine | 0.0318 | 0.0353 | 0.032800 |
| Alanine | 0.0815 | 0.0802 | 0.084600 |
| Valine | 0.0459 | 0.0471 | 0.050100 |
| Methionine | 0.0152 | 0.0145 | 0.016500 |
| Isoleucine | 0.0347 | 0.0349 | 0.036100 |
| Leucine | 0.1491 | 0.1439 | 0.152000 |
| Tyrosine | 0.0266 | 0.0305 | 0.028300 |
| Phenylalanine | 0.0552 | 0.0549 | 0.055600 |
| Histidine | 0.0277 | 0.0298 | 0.029500 |
| Lysine | 0.0218 | 0.0253 | 0.023600 |
| Arginine | 0.036700 | 0.041200 | 0.036300 |

Amino acid analysis of seed collected from the plants grown in the later experiment showed that the seed content of several agriculturally important amino acids could be increased by the presence of the gdhA gene (Table 6 E, F, G and H). Alanine, lysine and threonine contents were significantly increased by gdhA. Glutamate, arginine and phenylalanine were significantly decreased. Higher lysine and threonine content could increase the value of seed and grain crops used for animal feed. Lysine is a rate limiting amino acid in the diet of swine. Thus the present invention when placed in a swine diet will decrease the need to supplement the swine diet with added lysine. Thus a new use for the present invention is incorporation into corn grain and soybean grain to supply increased amounts of lysine to swine fed the diet by using grain of the present invention. Additionally, this gene in combination with other genes that overexpress the desired amino acid is contemplated in this invention.

Numerical differences in content were noted for most amino acids. gdhA increased alanine, aspartic acid, glycine, lysine, methionine, proline, serine, threonine and tyrosine; these increased contents increase the value of seed and grain crops used for animal feed. Methionine, is a rate limiting amino acid in the diet of poultry. Thus the present invention when placed in a swine diet will decrease the need to supplement the poultry diet with added methionine.

Comparison of amino acid contents of transgenic corn (Table 6I) showed that gdhA increased the content of apartic acid, threonine, serine, glycine, valine, methionine, tyrosine, histidine, lysine and arginine. These increased contents could increase the value of seed and grain crops used for animal feed. Comparison with the effects of gdhA expression in tobacco on seed amino acid content suggests that changes will be dependent on the plant species and genetic background in which gdhA has an effect.

EXAMPLE VI

Construction of Plasmids to Transfer *E. coli* gdhA to *Zea mays*.

The pBI121::GDH plasmid (shown in FIG. 4) was not particularly suitable for use in *Zea mays*. Thus, the plasmid pUBGPI (shown in FIG. 5) which is a vector suitable for transformation of *Zea mays* and foreign gene expression was employed.

The modified *E. coli* gdhA gene (shown in FIG. 6A as SEQ ID NO:12) was readily transferred to pUBGP1 to replace the GUS (uidA) gene by restriction digestion, gel purification of appropriate fragments and ligation as follows. Digestion of pBI121::GDH (shown in FIG. 4) with XbaI and EcoRI allowed recovery of gdhA::nosT as a 1.6 kbp fragment. Ligation with EcoRI XbaI digested pUC18 produced the plasmid pUCGDH1 which was amplified in *E. coli* DH5. Digestion of pUCGDH1 with PstI and EcoRII allowed recovery of the gdhA::nosT as a 1.6 kbp fragment. This mutagenized gdhA gene with the added linker restriction sites is shown in FIG. 7A (SEQ ID NO:14). Digestion of pUBGP1 with NcoI and SphI allowed recovery of the vector minus GUS::nosT as the 1.0 and 5.6 kbp fragments. Digestion of the 1.0 kbp fragment with PstI removed one NcoI site (and an inappropriate ATG codon). The 1.0 and 5.6 kbp pUBGPI fragments were ligated with the 1.6 kbp fragment from pBI121::GDH1 and an EcoRI/SphI adapter (shown in FIG. 8 as SEQ ID NOS:15–16).

The 3' EcoRI SphI adapter is between nosT and the plasmid for corn transformation. This gives pUBGDH1 (shown in FIG. 9) which was amplified in *E. coli* DH5.

The plasmid pUBGDH1 (shown in FIG. 9) was purified as DNA from *E. coli*, and 1 µg were used for transformation of *Zea mays* inbred line H99 by biolistics.

EXAMPLE VII

Construction of Plasmid to Target the *E. coli* gdbA to Chloroplasts in Corn.

Because the pBI121::GDH plasmid was not suitable for *Zea mays* transformation or gene expression, another plasmid vector was used to achieve gdhA gene transfer and expression. The 1.8 kbp SmaI to EcoRI fragment of pBI121::SSU::GDH1 was isolated and ligated with an EcoRI/SmaI adapter and SmaI digested pUC18. This produced the plasmid pUCSSUGDH1 which was amplified in *E. coli* DH5. Digestion of pUCSSUGDH1 with SmaI allowed recovery of the SSU::gdhA::nosT as a 1.8 kbp fragment (FIG. 7B). Digestion of pUBGP1 with NcoI and SphI allowed recovery of the vector minus GUS::nosT as the 1.0 and 5.6 kbp fragments. Digestion of the 1.0 kbp fragment with PstI removed the NcoI site (and an inappropriate ATG codon). The 1.0 and 5.6 kbp pUBGPI fragments were ligated with the 1.8 kbp fragment from pUCSSUGDH1 and an PstI/SmaI adapter to give pUBSSUGDH1 (FIG. 10) which was amplified in *E. coli* DH5.

The plasmid pUBSSUGDH1 was purified as DNA from *E. coli*, and 1 μg can be used for transformation of the *Zea mays* inbred line by any method.

EXAMPLE VIII

Method of Biochemical Analyses of Herbicide Resistance

Biochemical Analyses of Transformed Plants of the Above Examples.

Herbicide Resistance

Phosphinothricin (PPT) resistance was tested by initiating gdhA transformed leaf discs from greenhouse grown $R_o$ plants on MSO medium containing 1 mg/l BA, 0.1 mg/l NAA, 3% w/v sucrose and 7 g/l agar was supplemented with the herbicide IGNITE glufosinate at 0, 0.1, 1.0 or 10.0 mg/l active ingredient (a.i.) (5 replications of 1 $cm^2$ discs in individual culture tubes per concentration). Four weeks after initiation, cultures were photographed and the volume of leaf discs was measured.

$R_1$ Seed from gdbA transformed $R_0$ plants were also tested for herbicide resistance by germination and growth on MSO medium containing 3% w/v Sucrose and 7 g/l Agar supplemented with 0, 3, 9, 27 or 81 mg/l a.i. IGNITE glufosinate (30 seeds per plate with 3 replications per concentration) or 0, 1, 3, 10, 30 mg/l as noted in the text. Cultures were maintained at 25° C. with 16 hours of light. Four weeks after germination, cultures were photographed.

The gdhA transformed $R_0$ plants were also tested for herbicide resistance by painting leaves with 0, 3, 9, 27 or 81 mg/ml a.i. IGNITE glufosinate. Plants were maintained in the greenhouse. Four days after application chlorosis was scored.

Ammonium Toxicity Resistance

Resistance to ammonium toxicity in the absence of nitrate was measured by germinating transformed tobacco seed on agar solidified MSO medium excluding nitrogen. The medium was supplemented with 10, 30, 50, 70 or 100 mM ammonium chloride and seedlings were grown either with or without 30 mg/l sucrose. Ten to 15 seed were initiated per plate with 4 replications per concentration. Fresh and dry weights of 10 seedlings per plate were measured after 6 weeks on these media. Statistical analyses of these data were performed using SAS (SAS Institute Inc. Cary, N.C.).

The gohA transformed $R_0$ plants were also tested for ammonium resistance by painting leaves with 100, 300, 500, 700 or 1000 mM ammonium chloride. Plants were maintained in the greenhouse. Four days after application chlorosis was scored.

TABLE 7

Mean growth traits of adult transgenic corn FH24 inbred segregates in the greenhouse at Carbondale were significantly different.

| Plant Line | NADPH-GDH Activity (nM/mg/min) | Liberty Resistance % Applied[a] | Ear Leaf Area ($cm^3$) | Plant Height (cm) | Ear Leaf N Content (%) |
|---|---|---|---|---|---|
| LL9-37+[b] | 400 | 2 | 646 | 147 | 3.75 |
| LL9-37− | 0 | 0 | 330 | 113 | 3.72 |
| Prob.[c] | 0.0001 | 0.0001 | 0.03 | 0.1 | 0.05 |

[a]Liberty was painted onto a 1 $cm^3$ area of a mature leaf at 1%, 2%, 3% and 4% (v/v). Chlorosis after 4 weeks indicated susceptibility. The highest concentration to which plants were resistant is reported.
[b]LL9-37+ = GDH positive segregants from a gdhA transformant of corn.
LL9-37− = GDH negative segregants from a gdhA transformant of corn.
[b]Prob. = probability that the LL9-37+ and LL-37− segregates were significantly different.

This data show that in adult plants the height and ear leaf area of the gdhA transformant corn are significantly different than the isogeneic segregates lacking gdhA. However, nitrogen content is similar. The gdhA is efficient in increasing plant growth and yield. This test indicates that the present invention is tolerant at certain concentrations to glufosinate herbicides such as LIBERTY glufosinate. However, this test also indicates that the nitrogen content is similar. The gdhA is efficient in increasing plant growth and yield.

TABLE 8

Nitrogen runoff rate in tobacco and corn expressing gdhA.

| Plant Line | NADPH-GDH Activity (nM/mg/min) | Ammonium Concentration (mM) | Nitrite Concentration (mM) | Nitrate Concentration (mM) |
|---|---|---|---|---|
| Tobacco | | | | |
| BAR | 0 | 0.031 | 0.224 | 0.374 |
| 2A | 2046 | 0.022 | 0.189 | 0.298 |
| Corn | | | | |
| LL1-128− | 0 | 0.045 | 0.123 | 0.277 |
| LL1-128+ | 800 | 0.030 | 0.117 | 0.226 |

The corn plants used were isogeneic hybrid segregates derived from a cross from LL1-128 with A632. The presence or absence of gdhA was determined by leaf painting with 1% (w/v) LIBERTY glufosinate and spectrophotometric assay of GDH activity. Values presented are the means from eight plants. In each case, the gdhA transformants have increased the glutamate concentration in the plant roots significantly. The glutamine concentration also appears raised though not significantly.

EXAMPLE IX

I. Uptake Experiments

Seeds from gdhA transformed plants and seeds from uidA transformed plants were germinated on MSO medium without nitrogen. The medium was supplemented with 4% w/v sucrose. Two weeks after germination, the nitrogen starved seedlings were used to test whether the gdhA transformed seedlings were capable of absorbing radiolabelled methylammonium at a greater rate than the uidA transformed control plants. Fifteen seedlings were floated in the treatment solution (0.2 mM $CaCl_2$, 0.2 mM Mes pH 6.0, and 200

$\mu$M KCl) for 10 minutes. Radiolabelled 14C-methylammonium was then added to the treatment solution at a concentration of 1 mM. After 12, 24, 36, 48 or 60 minutes the labeled solution was aspirated and replaced with nonlabeled solution. The wash solution was aspirated after 2 minutes and the seedlings were transferred to scintillation vials. The seedlings were ground in 1 ml of water for 2 min. with a polytron (Tekmar Cinn. Ohio) to break open the cells. 2 mls of scintillation fluid was added per vial. The radioactivity absorbed by each sample was counted using an LS6000 scintillation counter (Beckman, Calif.) with an open window.

As indicated above in the previous example, the biochemical analysis of methylammonium uptake was tested. The transformed tobacco developed under the first couple of examples were employed in the uptake study. The results are shown in FIG. 11. The uptake of both the uidA and gdhA lines without 1 mM $NH_4$ was greatly enhanced in the time frame given.

II. Herbicide Resistance

A surprising aspect of the present gene in plant transformants is its tolerance to the herbicide phosphinothricin. The addition of the gdhA gene to either the PAT gene or the Bar gene apparently provides the plant with added resistance as shown by the plants' ability to continue to flourish and grow in increasing concentrations of herbicide. There are a number of commercially available herbicides that fit within the class of phosphinothricin herbicides.

The tobacco transformants of gdhA and uidA do not carry either the bar nor the PAT gene. A control used for comparison was a tobacco transformant containing the Bar gene. In contrast, the corn transformants all contain the PAT gene as the selectable marker. Therefore, the corn transformants show that the combination of phosphinothricin resistant gene(s) such as PAT in combination with the gdhA gene provides plants with increased resistance to chlorosis.

EXAMPLE X

GDH Activity of gdhA Transformants and Controls.

The tobacco transformants including the Bar transformant were developed either in examples provided earlier or by similar methods. The biochemical analysis was performed as indicated above. The results are as follows:

TABLE 9

Characteristics of the tobacco transgenic plant lines recovered.

| Strain/Gene | Explants Inoculated | gdhA[a] | PPT[b] |
|---|---|---|---|
| EHA101/gdhA | 30 | 12 | 10 |
| LBA4404/gdhA | 30 | 2 | 1 |
| LBA4404/gdhA | 15 | 0 | 0 |
| EHA101/uidA | 15 | 0 | 0 |
| LBA4404/bar | 15 | 0 | 4 |

[a] = positive bands after electrophoresis of crude extract on 5% polyacrylamide gel followed by NADP-dependent tetrazolium staining of GDH isozymes.
[b] = Seedlings resistant to 3 $\mu$g a.i./ml PPT.

Clearly, both the LBA4404/bar and EHA100/gdhA lines as seedlings were resistant to 3 $\mu$g a.i./ml PPT. Thus, the tobacco plants can be sprayed in a field with weeds with the PPT herbicide and at least at the indicated levels of PPT will not have chlorosis evidenced.

EXAMPLE XI

Volume of tobacco callus formed in present of various levels of PPT. The transformants of the earlier examples were tested in various herbicide concentrations.

TABLE 10

Mean volume of tobacco callus[a] with various concentrations of the herbicide (PPT).

| Herbicide conc. mg. a.i./l | 2A (gdhA) (cm³) | n[b] | 8₂ (gdhA) (cm³) | n | 9₁ (gdhA) (cm³) | n | 7B (uidA) (cm³) | n | Significance[c] |
|---|---|---|---|---|---|---|---|---|---|
| 0.0 | 20929.4[d] | 5 | 17275.0 | 5 | 20763.2 | 5 | 16056.9 | 3 | NS |
| 0.1 | 12873.2 | 5 | 11489.0 | 3 | 14949.5 | 4 | 2515.9 | 2 | ** |
| 1.0 | 3828.7 | 4 | 6478.1 | 5 | 9634.0 | 5 | 0.0 | 4 | ** |
| 10.0 | 0.0 | 5 | 0.0 | 5 | 0.0 | 5 | 0.0 | 4 | NS |

[a]Greenhouse grown leaf tissue from gdhA or uidA $R_0$ transformed plants were initiated on MS medium in culture tubes and incubated in the light at 25° C. for 4 weeks before volume was calculated.
[b]n = number of explants
[c]** = significant at the 1% level, NS = nonsignificant
[d]volume was calculated using the formula 3.14 r²h The evidence clearly indicates that the volume of callus of uidA tobacco callus in PPT is significantly less then callus of the gdhA tobacco.

TABLE 11

Dry weight of $R_1$ leaf derived callus[a] with various concentrations of the herbicide (PPT).

| Transformed Lines | Callus GDH activity (nmol/mg[a]/min) | Dry weight (mg) at herbicide concentration (mg a.i./l) | | |
|---|---|---|---|---|
| | | 0 | 1 | 3 |
| BAR | 0 | 217 (8)[b] | 191 (7) | 185 (6) |
| 9₁ | 1640 | 267 (8) | 215 (10) | 48 (9) |
| 9X | 1610 | 227 (10) | 167 (9) | 30 (10) |
| 2A | 1510 | 269 (9) | 159 (10) | 23 (10) |
| 9₂N | 570 | 269 (9) | 168 (10) | 48 (10) |
| 9₅W | 330 | 239 (9) | 124 (9) | 13 (9) |

TABLE 11-continued

Dry weight of $R_1$ leaf derived callus[a]
with various concentrations of the herbicide (PPT).

| Transformed Lines | Callus GDH activity (nmol/ mg[a]/min) | Dry weight (mg) at herbicide concentration (mg a.i./l) | | |
|---|---|---|---|---|
| | | 0 | 1 | 3 |
| $9_4R$ | 290 | 256 (9) | 94 (5) | 11 (10) |
| 7B | 0 | 215 (10) | 33 (8) | 4 (9) |
| Significance | LSD.05 | 56 | 34 | 12 |
| | LSD.01 | 83 | 51 | 18 |
| Standard Deviation | | 526 | 61 | 48 |

[a]Greenhouse grown leaf tissue from gdhA or uidA $R_1$ transformed plants were initiated on MS medium in culture tubes and incubated in the light at 25° C. for 4 weeks before GDH assays. Specific activity per mg of soluble protein with 10 mM ammonium chloride.
[b]number of explants is shown in parentheses Volume of tobacco callus formed in the presence of various concentrations of the herbicide LIBERTY glufosinate clearly indicate that callus volume is dependent on the level of expression of gdhA as detected by GDH enzyme assays.

EXAMPLE XII
Volume of Corn Callus in Present of PPT

The volume of corn callus by volume was calculated in light of different transformant lines. Unlike the previous example, there is no control line that does not carry a PAT gene. Both the gdhA and the uidA transformants contain PAT which has resistance to PPT.

EXAMPLE XIII
RO Plants Herbicide Resistance

The results of herbicide resistance in $R_0$ corn and tobacco transformants and the gdhA activity as measured by NADPH-GDH was compared. The following results were gathered.

TABLE 12

Herbicide resistance concentration dependence and GDH activity in R0 plants expressing gdhA.

| Plant Line | NADPH-GDH Activity (nM/mg/min) | PPT concentration (mg a.i/ml) | | | | |
|---|---|---|---|---|---|---|
| | | 0 | 1 | 2 | 3 | 4 |
| a, Tobacco | | | | | | |
| UID | 0 | + | − | − | nd | nd |
| 2A | 2046 | + | + | + | nd | nd |
| 82 | 2060 | + | + | + | nd | nd |
| 91 | 1840 | + | + | + | nd | nd |
| 9Z1 | 1760 | + | + | + | nd | nd |
| BAR | 0 | + | + | + | nd | nd |
| b, Corn (all contain the pat gene) | | | | | | |
| LL3-775#131 | 1310 | + | + | + | + | + |
| LL2-63#12 | 500 | + | + | + | + | − |
| LL2-63#15 | 300 | + | + | + | − | − |
| LL2-63#9 | 150 | + | +/− | − | − | − |
| LL2-63#6 | 0 | + | − | − | − | − | nd not determined
+ resistance to chlorosis
− chlorotic 2–3 weeks after treatment The above experiment clearly indicates the herbicide tolerance in the plants of the present invention is increased over the control plants. The results show that transformants without the gdhA gene provide no protection against the herbicide, The transformant line 9Z1 evidences the least amount of NADPH-GDH activity and it still gives resistance to 2% LIBERTY glufosinate solution.

Activity levels of NADPH-GDH of 1000 and over provided PPT resistance in tobacco. In corn, which has added PPT resistance, the controls were not resistant to 1% liberty leaf paint. However, as activity levels of GDH increased so did resistance to LIBERTY glufosinate. The combination of the pat gene and gdhA gene in corn shows even a 4% solution of LIBERTY glufosinate can be resisted (line LL3-775#131).

EXAMPLE XIV

Progeny of corn plants containing gdhA gene and either the Bar gene or the PAT gene which are bred and developed from the seeds of the $R_0$ plants of the examples above can be planted in a field. This field could then be sprayed for weeds with a phosphinothricin herbicide such as IGNITE glufosinate. This is a method of increasing plant growth. This herbicide spraying would eliminate most of the undesirable vegetation and the plants containing the gdhA gene would survive and increase growth. Alternatively, the corn plants can be transformed with the gdhA gene only and not include the selectable marker of either Bar or PAT. This transformant would be expected to survive the spraying and also show increased growth though it may be slightly less tolerant.

$R_1$ Tobacco Seedling Growth After Four Weeks on LIBERTY Glufosinate (PPT).

The experiment had a bar only line, a gdhA (line 2A) and uidA (line 7A) transformed $R_1$ seedlings germinated on agar solidified MS medium supplemented with 3 mg/l a.i. of the herbicide LIBERTY glufosinate (PPT). The bar only line filled about 90% of the petri dish with seedlings, the gdhA (line 2A) line filled about 40% of the petri dish with seedlings, and uidA (line 7A) line filled about 10% of the petri dish with seedlings.

Eight Week Old $R_1$ Tobacco Plants

Eight week old $R_1$ tobacco plants one week after they were sprayed to runoff with a 1% solution of the herbicide LIBERTY glufosinate were visually examined. line 7B (uidA) 0 nmol/mg/min GDH activity had obvious leaf death and had turned a light green color. Line $9_1$ (gdhA) 1840 nmol/mg/min GDH activity had some leaf spotting but had not turned a light green; line 2A (gdhA) 2040 nmol/mg/min GDH activity; line $8_2$ (gdhA) 2060 nmol/min/mg GDH activity both appeared healthier then Lines $9_1$ and $9Z_1$ but still had some though less then $9_1$ and $9Z_1$ leaf spotting; line $9Z_1$ (gdhA) 1760 nmol/min/mg GDH activity had some leaf spotting but had not turned a light green; line BAR (bar) 0 nmol/mg/min GDH activity was significantly darker green and showed little to no leaf spotting.

Eight Week Old $R_1$ Inbred Corn Plants

Eight week old inbred corn plants were visually examined one week after they were leaf painted with a 1%, 2%, 3% or 4% (v/v) solution of the herbicide LIBERTY glufosinate. Line LL3-755#131 (gdhA) having 1310 nmol/mg/min GDH activity showed no visible effects to 1–3% and only a barely discernible light browning in a small area at 4%. Line LL2-63#12 (gdhA) 500 nmol/mg/min GDH activity showed no apparent effects at 1%, slight browning (significantly more then line LL3-755#131at 4%) at 2% and about 60% browning at 3% and 100% browning at 4%. Line LL2-63#6 (no transgene sergeant otherwise isogeneic to LL2-63#12) 0 nmol/mg/min GDH activity showed 100% browning in the painted area at land 2% and extended browning outside of the area at 3% and 4%. These plant correspond to those described in Table 13.

The gdhA gene can be transformed into crop plants that would not be expected to be effected by the herbicide PPT. This would allow better growth of these plants in fields that are sprayed or in those that are not sprayed.

EXAMPLE XV

Improved crop nitrogen assimilation can reduce environmental contamination by nitrates. Specialty corn hybrids for planting in watershed areas or for biofuel feedstocks will be developed.

Nitrogen Runoff Determinations

Plants were fertilized with 1 liter of 10 mM ammonium nitrate and subsequently not watered or fertilized. After 48 hours, the root system was flushed with 10 liters of water and the runoff water from each pot collected. The ammonia concentration in each run-off water sample was determined by Nesslerization. Briefly, 1 ml. of sample was mixed with 1 ml. of 0.2% gum acacia solution, 1 ml. of Nesslers reagent, 7 ml. of water. After 20 minutes, the absorbance was determined at 420 nm. The nitrite concentration was determined by mixing 2 ml. of sample. 5 ml. of sulphanilic acid solution and 5 ml. of alpha-napathyl amine solution. After 30–60 minutes, the absorbance was determined at 540 nm. The nitrate concentration was determined by the 4-methylumbelliferone method. Briefly, 0.5 ml. of sample was mixed with 50 $\mu$l of 1 M sulfamic acid and heated to 100 C for 5 minutes. On ice 10 ml. of 4.4 M ammonia. After 20 minutes at room temperature, the absorbance was determined at 540 nm.

TABLE 13

Nitrogen runoff rate in tobacco and corn expressing gdhA.

| Plant Line | NADPH-GDH Activity (nM/mg/min) | Ammonium Concentration (mM) | Nitrate Concentration (mM) | Nitrate Concentration (mM) |
|---|---|---|---|---|
| a, Tobacco | | | | |
| BAR | 0 | 0.3 | 0.3 | 0.4 |
| 2A | 2046 | 0.2 | 0.1 | 0.2 |
| b, Corn | | | | |
| DL1 | 0 | 0.2 | 0.3 | 0.5 |
| LL1 | 800 | 0.1 | 0.1 | 0.2 |

These results show that the gdhA gene can be used to decrease the nitrogen content of runoff-water. The increased assimilation by plant roots results in less nitrogen to be available for leaching.

Significance

Biofuels/Watershed Premium

Unassimilated nitrogen is converted to nitrate and much is leached from the soil and into groundwater. The EPA is already considering setting limits on nitrogen use in watershed areas. Agricultural inputs contribute to nitrogen contamination in Illinois drinking water, particularly in the North Central region. More than 18 community water supplies and 25% of the 360,000 private wells contain concentrations of nitrogen above the EPA limits. Improving corn nitrogen assimilation with foreign transgenes may reduce nitrogen loss by increasing assimilation. Attempts to develop such corn might be used to delay restrictive legislation and increase support for corn derived biofuels. Approximately 20% of Illinois farmland is in watershed areas. An increase of 10% in the corn derived ethanol as oxygenate addition to gasoline would double the demand for corn and would lead to higher corn prices.

Health Benefits

The association between dietary nitrates and several cancers is weak but positive (Moller et. al. 1990). Groundwater consumption can be a significant source of dietary nitrates in Illinois (Lee and Neilson 1987). Reducing groundwater contamination by nitrates may have a small beneficial effect on the rate of cancers. Infants 9–6 years old are at particular risk from dietary nitrates because nitrate reacts strongly with their blood hemoglobin causing methemoglobinemia, a condition similar to carbon monoxide poisoning in adults (Marschner, 1995). Bottled water is periodically recommended for infants in 18 Illinois communities with high nitrogen in their water supplies. Dietary nitrates are associated with higher abortion rates (Prins, 1983).

Environmental Premium

A health food or environmental premium on the market price of improved corn might be developed by marketing strategies. This might also lead to increased utilization. If a 1 cent per bushel premium for "low nitrogen impact" corn developed and Illinois farmers grew 1.74 billion bushels then profits would increase $17.4 million in Illinois.

Reduced Producer Losses

Assuming a 10% nitrogen loss, 175 lb./acre use, 10 cents/lb. cost, and 13 million acres planted then income losses are: 0.1×175×10×13,000,000=$23 million or $1.75 per acre. Although annual producer losses may approach $23 million per year in Illinois this is likely to vary depending on weather, soil types and cultural practices. The technology proposed might reduce producer expenses some part of that $23 million per year in Illinois.

EXAMPLE XVI

Altered Seed Composition

Using the $R_0$ plants produced by the previous examples, the plants can be further modified to include genes that alter seed composition. A number of these types of genes are known in the art. These genes make altered hybrids. Altered seed composition leads to several specialty corn hybrids and products. High protein corn could be produced by increasing nitrogen assimilation. High sucrose corn or increased starch accumulation could be produced by simultaneous manipulation of carbon and nitrogen metabolism. The gdhA gene used in association with genes that alter starch content or chemical form or sugar content or form to promote alterations in plant composition.

TABLE 14

The effect of gdhA on plant seed carbohydrate composition.
Tobacco grown with 75 lb. per acre anhydrous N.

| | GDH+ Mean | GDH− Mean |
|---|---|---|
| Starch 1 | 0.72100 | 0.32250 |
| | 0 | 0 |
| Starch 2 | 0.03325 | 0.03250 |
| (o/n) | 0 | 0 |
| Red | 3.56375 | 3.66750 |
| Sugar | 0 | 0 |
| Pentose | 0.45825 | 0.18300 |
| | 0 | 0 |
| Hexose | 0.57500 | 0.84700 |
| | 0 | 0 |

TABLE 14-continued

The effect of gdhA on plant seed carbohydrate composition.
Tobacco grown with 75 lb. per acre anhydrous N.

|  | GDH+ Mean | GDH− Mean |
|---|---|---|
| Sucrose | 1.033250 | 1.030000 |

This experiment shows that starch content was much higher in the GDH+ transgenic plants than those lacking gdhA. Therefore, gdhA can be used to increase starch content of crops such as corn, potato and tomato to improve their food processing characteristics and the % of extractable starch. No additional starch could be extracted by the overnight treatment and the GDH+ and GDH− lines did not differ. The sucrose and total reducing sugar contents are not affected by the increase in starch content caused by gdhA. However, there are more pentose sugars and less hexose sugars in the gdhA transgenic plants. These results show that gdhA can be used to alter the type of sugar of crops such as corn, potato, tomato, sugar beet and sugar cane to improve their food processing characteristics.

TABLE 15

The effect of gdhA on plant seed carbohydrate composition.
Tobacco grown with 150 lb. per acre anhydrous N.

|  | GDH+ Mean | GDH− Mean |
|---|---|---|
| Starch 1 | 0.846750 | 0.606500 |
| Starch 2 (o/n) | 0.032750 | 0.051500 |
| Red Sugar | 3.643000 | 3.530600 |
| Pentose | 0.583000 | 0.141250 |
| Hexose | 0.736500 | 0.470000 |
| Sucrose | 1.319500 | 0.611250 |

This experiment shows that at higher nitrogen input (150 lb. per acre) starch content was much higher in the GDH+ transgenic plants than those lacking gdhA. Therefore, gdhA can be used to increase starch content of crops such as corn, potato and tomato to improve their food processing characteristics and the % of extractable starch. Some additional starch could be extracted by the overnight treatment and the GDH+ and GDH− lines did not differ significantly. The sucrose and total reducing sugar contents are not affected by the increase in starch content caused by gdhA. However, there are more pentose sugars, hexose sugars and sucrose in the gdhA transgenic plants. These results show that gdhA can be used to alter the amount of sugar at high N input rates. Therefore gdhA can be use to increase the value of crops such as corn, potato, tomato, sugar beet and sugar cane and improve their food processing characteristics.

The use of gdhA in association with other transgenes, mutants or cultivars that affect starch and sucrose content is envisioned. Cotransformation or crossing of transgenic plants to contain gdhA and genes encoding ADPglucose pyrophosphorylase (glgC), cytoplasmic and chloroplastic fructose-1-6-bisphosphatase, sucrose phoshate synthase. triose phosphate tanslocator, phosphglucose isomerase, Fructose-6-phosphate kinase, UDP glucose pyrophosphorylase, invertase, phosphofructoldnase, ribulose bisphosphate caiboxylase and the glucose tansports is envisioned within the scope of the present invention (Stitt and Sonnewald, 1995, Annu. Rev. Plant Physiol. Plant Mol. Biol. 46:341–368).

We claim:

1. A method of growing a transgenic crop plant in the presence of phosphinothricin herbicide, wherein the growth of said transgenic crop plant is resistant to an herbicide of the phosphinothricin class due to being transformed with a DNA sequence encoding a bacterial NADP-specific glutamate dehydrogenase enzyme, said enzyme conferring on said transgenic crop plant the ability to grow in the presence of an amount of said herbicide of the phosphinothricin class sufficient to inhibit growth of a crop plant not transformed with said DNA sequence, said method comprising: applying to a field in which said transgenic crop plant is growing an effective amount of said herbicide of the phosphinothricin class sufficient to inhibit growth of said crop plant not transformed with said DNA sequence.

2. A method according to claim 1 wherein said DNA sequence comprises the Kozac consensus sequence.

3. A method according to claim 1 wherein applying said herbicide of the phosphinothricin class is combined with applying to said field an effective amount of a second herbicide.

4. A method according to claim 1 wherein said crop plant is selected from the group consisting of corn, cotton, brassica, soybean, wheat and rice.

5. Transgenic plant cells and progeny thereof comprising an expression cassette comprising:
  1) a transcription initiation region functional in the plant cells;
  2) a DNA sequence that encodes a bacterial NADP-specific GDH enzyme; and
  3) a transcription termination region functional in said plant cells,
    wherein said expression cassette imparts a detectable level of herbicide resistance to the phosphinothricin class of herbicides.

6. Cells according to claim 5 wherein at least one of said transcription region and said transcription termination region is not naturally associated with said DNA sequence.

7. Cells according to claim 5 wherein said DNA sequence is from *E. coli*.

8. Cells according to claim 5 wherein said DNA sequence is modified to enhance expression in plant cells.

9. Cells according to claim 5 wherein the DNA sequence of SEQ ID NO:11 encodes the amino acid sequence of.

10. Cells according to claim 5 wherein the expression cassette comprises a chloroplast transit peptide adapted to target the enzyme to the chloroplasts.

11. Cells according to claim 5 wherein said transcription initiation region is constitutive.

12. Cells according to claim 5 wherein said transcription initiation region is organ specific.

13. A cell culture of cells according to claim 5 wherein said expression cassette further comprising a marker gene wherein the cells grow in a culture medium which includes a herbicide which is in the phosphinothricin class.

14. A cell culture of cells according to claim 5 further comprising a marker gene that is capable of growth in a culture medium which includes a herbicide which is not a phosphinothricin class.

15. A cell culture of claim 13 wherein said herbicide is bialaphos.

16. A transgenic plant wherein the growth of said transgenic plant is resistant to an herbicide of the phosphinothricin class due to being transformed with a gene encoding a bacterial NADP-specific glutamate dehydrogenase enzyme, said enzyme conferring on said transgenic plant the ability to grow in the presence of an amount of a phosphinothricin class herbicide sufficient to inhibit growth of said plant not transformed with said gene.

17. A transgenic plant according to claim 16 wherein said plant is a dicot.

18. A transgenic plant according to claim 16 wherein said plant is a monocot.

19. A transgenic plant according to claim 18 wherein said plant is *Zea mays*.

20. A transgenic plant according to claim 17 wherein said plant is selected from the group consisting of brassica, cotton, soybean and tobacco.

21. A transgenic plant according to claim 16 wherein said plant produces seeds and said plant is also transformed with a gene that alters a property of said seeds selected from the group consisting of the protein content and the oil content of said seeds.

22. A transformed corn plant containing a bacterial NADP-specific glutamate dehydrogenase gene.

23. A plant containing a transgene encoding a bacterial NADP-specific glutamate dehydrogenase gene.

24. Cells according to claim 5 wherein the DNA sequence is SEQ ID NO:1.

25. Cells according to claim 5 wherein the DNA sequence is SEQ ID NO:2.

26. A transformed corn plant according to claim 22 that is resistant to a herbicide of the phosphinothricin class, wherein said plant further contains a second transgene.

27. A method of growing a transgenic crop plant in the presence of bialaphos herbicide, wherein the growth of said transgenic crop plant is resistant to bialaphos due to being transformed with a gene encoding a bacterial NADP-specific glutamate dehydrogenase enzyme, said enzyme conferring on said transgenic crop plant the ability to grow in the presence of an amount of bialaphos sufficient to inhibit growth of a crop plant not transformed with said gene, said method comprising: applying to a field in which said transgenic crop plant is growing an effective amount of bialaphos sufficient to inhibit growth of said crop plant not transformed with said gene.

28. Transgenic plant cells and progeny thereof comprising an expression cassette comprising:
 1) a transcription initiation region functional in said plant cells,
 2) a DNA sequence that encodes a bacterial NADP-specific glutamate dehydrogenase enzyme, and
 3) a transcription termination region functional in said plant cells;
  wherein said expression cassette imparts a detectable level of resistance to bialaphos.

29. A transgenic plant, wherein the growth of said transgenic plant is resistant to bialaphos due to being transformed with a gene encoding a bacterial NADP-specific glutamate dehydrogenase enzyme, said enzyme conferring on said transgenic plant the ability to grow in the presence of an amount of bialaphos sufficient to inhibit growth of a plant not transformed with said gene.

30. A method of growing a transgenic crop plant in the presence of glufosinate herbicide, wherein the growth of said transgenic crop plant is resistant to glufosinate due to being transformed with a gene encoding a bacterial NADP-specific glutamate dehydrogenase enzyme, said enzyme conferring on said transgenic crop plant the ability to grow in the presence of an amount of glufosinate sufficient to inhibit growth of a crop plant not transformed with said gene, said method comprising: applying to a field in which said transgenic crop plant is growing an effective amount of glufosinate sufficient to inhibit growth of said crop plant not transformed with said gene.

31. Transgenic plant cells and progeny thereof comprising an expression cassette comprising:
 1) a transcription initiation region functional in said plant cells,
 2) a DNA sequence that encodes a bacterial NADP-specific glutamate dehydrogenase enzyme, and
 3) a transcription termination region functional in said plant cells;
  wherein said expression cassette imparts a detectable level of resistance to glufosinate.

32. A transgenic plant, wherein the growth of said transgenic plant is resistant to glufosinate due to being transformed with a gene encoding a bacterial NADP-specific glutamate dehydrogenase enzyme, said enzyme conferring on said transgenic plant the ability to grow in the presence of an amount of glufosinate sufficient to inhibit growth of a plant not transformed with said gene.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1659 bases
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TCGAAAACTG CAAAAGCACA TGACATAAAC AACATAAGCA CAATCGTATT AATATATAAG      60

GGTTTTATAT CTATGGATCA GACATATTCT CTGGAGTCAT TCCTCAACCA TGTCCAAAAG     120

CGCGACCCGA ATCAAACCGA GTTCGCGCAA GCCGTTCGTG AAGTAATGAC CACACTCTGG     180

CCTTTTCTTG AACAAAATCC AAAATATCGC CAGATGTCAT TACTGGAGCG TCTGGTTGAA     240
```

```
CCGGAGCGCG TGATCCAGTT TCGCGTGGTA TGGGTTGATG ATCGCAACCA GATACAGGTC      300

AACCGTGCAT GGCGTGTGCA GTTCAGCTCT GCCATCGGCC CGTACAAAGG CGGTATGCGC      360

TTCCATCCGT CAGTTAACCT TTCCATTCTC AAATTCCTCG GCTTTGAACA AACCTTCAAA      420

AATGCCCTGA CTACTCTGCC GATGGGCGGT GGTAAAGGCG GCAGCGATTT CGATCCGAAA      480

GGAAAAAGCG AAGGTGAAGT GATGCGTTTT TGCCAGGCGC TGATGACTGA ACTGTATCGC      540

CACCTGGGCG CGGATACCGA CGTTCCGGCA GGTGATATCG GGGTTGGTGG TCGTGAAGTC      600

GGCTTTATGG CGGGGATGAT GAAAAAGCTC TCCAACAATA CCGCCTGCGT CTTCACCGGT      660

AAGGGCCTTT CATTTGGCGG CAGTCTTATT CGCCCGGAAG CTACCGGCTA CGGTCTGGTT      720

TATTTCACAG AAGCAATGCT AAAACGCCAC GGTATGGGTT TTGAAGGGAT GCGCGTTTCC      780

GTTTCTGGCT CCGGCAACGT CGCCCAGTAC GCTATCGAAA AGCGATGGA ATTTGGTGCT      840

CGTGTGATCA CTGCGTCAGA CTCCAGCGGC ACTGTAGTTG ATGAAAGCGG ATTCACGAAA      900

GAGAAACTGG CACGTCTTAT CGAAATCAAA GCCAGCCGCG ATGGTCGAGT GGCAGATTAC      960

GCCAAAGAAT TTGGTCTGGT CTATCTCGAA GGCCAACAGC CGTGGTCTCT ACCGGTTGAT     1020

ATCGCCCTGC CTTGCGCCAC CCAGAATGAA CTGGATGTTG ACGCCGCGCA TCAGCTTATC     1080

GCTAATGGCG TTAAAGCCGT CGCCGAAGGG CAAATATGC CGACCACCAT CGAAGCGACT     1140

GAACTGTTCC AGCAGGCAGG CGTACTATTT GCACCGGGTA AGCGGCTAA TGCTGGTGGC     1200

GTCGCTACAT CGGGCCTGGA AATGGCACAA AACGCTGCGC GCCTGGGCTG AAAGCCGAG     1260

AAAGTTGACG CACGTTTGCA TCACATCATG CTGGATATCC ACCATGCCTG TGTTGACCAT     1320

GGTGGTGAAG GTGAGCAAAC CAACTACGTG CAGGGCGCGA ACATTGCCGG TTTTGTGAAG     1380

GTTGCCGATG CGATGCTGGC GCAGGGTGTG ATTTAAGTTG TAAATGCCTG ATGGCGCTAC     1440

GCTTATCAGG CCTACAAATG GCACAATTC ATTGCAGTTA CGCTCTAATG TAGGCCGGGC     1500

AAGCGCAGCG CCCCCGGCAA ATTTCAGGC GTTTATGAGT ATTTAACGGA TGATGCTCCC     1560

CACGGAACAT TTCTTATGGG CCAACGGCAT TTCTTACTGT AGTGCTCCCA AAACTGCTTG     1620

TCGTAACGAT AACACGCTTC AAGTTCAGCA TCCGTTAAC                            1659

(2) INFORMATION FOR SEQ ID NO:2:

(i) SEQUENCE CHARACTERISTICS:
        (A) LENGTH: 1659 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO:2:

TCGAAAACTG CAAAAGCACA TGACATAAAC AACATAAGCA CAATCGTATT AATATATAAG       60

GGTTCTAGAA CAATGGATCA GACATATTCT CTGGAGTCAT TCCTCAACCA TGTCCAAAAG      120

CGCGACCCGA ATCAAACCGA GTTCGCGCAA GCCGTTCGTG AAGTAATGAC CACACTCTGG      180

CCTTTTCTTG AACAAAATCC AAAATATCGC CAGATGTCAT TACTGGAGCG TCTGGTTGAA      240

CCGGAGCGCG TGATCCAGTT TCGCGTGGTA TGGGTTGATG ATCGCAACCA GATACAGGTC      300

AACCGTGCAT GGCGTGTGCA GTTCAGCTCT GCCATCGGCC CGTACAAAGG CGGTATGCGC      360

TTCCATCCGT CAGTTAACCT TTCCATTCTC AAATTCCTCG GCTTTGAACA AACCTTCAAA      420

AATGCCCTGA CTACTCTGCC GATGGGCGGT GGTAAAGGCG GCAGCGATTT CGATCCGAAA      480
```

```
GGAAAAAGCG AAGGTGAAGT GATGCGTTTT TGCCAGGCGC TGATGACTGA ACTGTATCGC    540

CACCTGGGCG CGGATACCGA CGTTCCGGCA GGTGATATCG GGGTTGGTGG TCGTGAAGTC    600

GGCTTTATGG CGGGGATGAT GAAAAAGCTC TCCAACAATA CCGCCTGCGT CTTCACCGGT    660

AAGGGCCTTT CATTTGGCGG CAGTCTTATT CGCCCGGAAG CTACCGGCTA CGGTCTGGTT    720

TATTTCACAG AAGCAATGCT AAAACGCCAC GGTATGGGTT TTGAAGGGAT GCGCGTTTCC    780

GTTTCTGGCT CCGGCAACGT CGCCCAGTAC GCTATCGAAA AAGCGATGGA ATTTGGTGCT    840

CGTGTGATCA CTGCGTCAGA CTCCAGCGGC ACTGTAGTTG ATGAAAGCGG ATTCACGAAA    900

GAGAAACTGG CACGTCTTAT CGAAATCAAA GCCAGCCGCG ATGGTCGAGT GGCAGATTAC    960

GCCAAAGAAT TTGGTCTGGT CTATCTCGAA GGCCAACAGC CGTGGTCTCT ACCGGTTGAT   1020

ATCGCCCTGC CTTGCGCCAC CCAGAATGAA CTGGATGTTG ACGCCGCGCA TCAGCTTATC   1080

GCTAATGGCG TTAAAGCCGT CGCCGAAGGG GCAAATATGC CGACCACCAT CGAAGCGACT   1140

GAACTGTTCC AGCAGGCAGG CGTACTATTT GCACCGGGTA AAGCGGCTAA TGCTGGTGGC   1200

GTCGCTACAT CGGGCCTGGA AATGGCACAA AACGCTGCGC GCCTGGGCTG AAAGCCGAG    1260

AAAGTTGACG CACGTTTGCA TCACATCATG CTGGATATCC ACCATGCCTG TGTTGACCAT   1320

GGTGGTGAAG GTGAGCAAAC CAACTACGTG CAGGGCGCGA ACATTGCCGG TTTTGTGAAG   1380

GTTGCCGATG CGATGCTGGC GCAGGGTGTG ATTTAAGTTG TAAATGCCTG ATGGCGCTAC   1440

GCTTATCAGG CCTACAAATG GCACAATTC ATTGCAGTTA CGCTCTAATG TAGGCCGGGC    1500

AAGCGCAGCG CCCCCGGCAA AATTTCAGGC GTTTATGAGT ATTTAACGGA TGATGCTCCC   1560

CACGGAACAT TTCTTATGGG CCAACGGCAT TTCTTACTGT AGTGCTCCCA AAACTGCTTG   1620

TCGTAACGAT AACACGCTTC AAGTTCAGCA TCCGTTAAC                          1659

(2) INFORMATION FOR SEQ ID NO:3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GGGTTCTAGA ACAATGGATC AGACATATTC TCTGGAG                             37

(2) INFORMATION FOR SEQ ID NO:4:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CATTGAGCTC TTAAATCACA CCCTGCGCCA GCATC                               35

(2) INFORMATION FOR SEQ ID NO:5:

(i) SEQUENCE CHARACTERISTICS:
        (A) LENGTH: 49 bases
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:5:

GGGTTTTATA TCTATGGATC AGACATATTC TCTGGAGTCA TTCCTCAAC          49

(2) INFORMATION FOR SEQ ID NO:6:

(i) SEQUENCE CHARACTERISTICS:
        (A) LENGTH: 49 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CTTGAGGAAT GACACCAGAG AATATGTCTG ATCCATAGAT ATAAAACCC          49

(2) INFORMATION FOR SEQ ID NO:7:

(i) SEQUENCE CHARACTERISTICS:
        (A) LENGTH: 12 residues
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:7:

Met Asp Gln Thr Tyr Ser Leu Glu Ser Phe Leu Asn
1               5                   10

(2) INFORMATION FOR SEQ ID NO:8:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TGCGATGCTG GCGCAGGGTG AGATTTAAGT TGTAAATG                      38

(2) INFORMATION FOR SEQ ID NO:9:

(i) SEQUENCE CHARACTERISTICS:
        (A) LENGTH: 38 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CATTTACAAC TTAAATCTCA CCCTGCGCCA GCATCGCC                      38

(2) INFORMATION FOR SEQ ID NO:10:

(i) SEQUENCE CHARACTERISTICS:
        (A) LENGTH: 8 residues
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:10:

Ala Met Leu Ala Gln Gly Val Ile
1               5

(2) INFORMATION FOR SEQ ID NO:11:

(i) SEQUENCE CHARACTERISTICS:
        (A) LENGTH: 447 residues
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:11:

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
50                  55                      60

Val Val Trp Val Asp Asp Arg Asn Gln Ile Gln Val Asn Arg Ala Trp
65                      70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
            115                 120                 125

Gly Gly Ser Asp Phe Asp Pro Lys Gly Lys Ser Glu Gly Glu Val Met
            130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
            195                 200                 205

Glu Ala Thr Gly Tyr Gly Leu Val Tyr Phe Thr Glu Ala Met Leu Lys
210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
            275                 280                 285

Arg Asp Gly Arg Val Ala Asp Tyr Ala Lys Glu Phe Gly Leu Val Tyr
            290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile

|   | 325 |   |   |   | 330 |   |   |   | 335 |   |   |
|---|---|---|---|---|---|---|---|---|---|---|---|

Ala Asn Gly Val Lys Ala Val Ala Glu Gly Ala Asn Met Pro Thr Thr
              340              345              350

Ile Glu Ala Thr Glu Leu Phe Gln Gln Ala Gly Val Leu Phe Ala Pro
   355               360              365

Gly Lys Ala Ala Asn Ala Gly Gly Val Ala Thr Ser Gly Leu Glu Met
370              375              380

Ala Gln Asn Ala Ala Arg Leu Gly Trp Lys Ala Glu Lys Val Asp Ala
385              390              395              400

Arg Leu His His Ile Met Leu Asp Ile His Ala Cys Val Asp His
              405              410              415

Gly Gly Glu Gly Glu Gln Thr Asn Tyr Val Gln Gly Ala Asn Ile Ala
              420              425              430

Gly Phe Val Lys Val Ala Asp Ala Met Leu Ala Gln Gly Val Ile
              435              440              445

(2) INFORMATION FOR SEQ ID NO:12:

(i) SEQUENCE CHARACTERISTICS:
        (A) LENGTH: 1489 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
TCTAGAACAA TGGATCAGAC ATATTCTCTG GAGTCATTCC TCAACCATGT CCAAAAGCGC      60
GACCCGAATC AAACCGAGTT CGCGCAAGCC GTTCGTGAAG TAATGACCAC ACTCTGGCCT     120
TTTCTTGAAC AAAATCCAAA ATATCGCCAG ATGTCATTAC TGGAGCGTCT GGTTGAACCG     180
GAGCGCGTGA TCCAGTTTCG CGTGGTATGG GTTGATGATC GCAACCAGAT ACAGGTCAAC     240
CGTGCATGGC GTGTGCAGTT CAGCTCTGCC ATCGGCCCGT ACAAAGGCGG TATGCGCTTC     300
CATCCGTCAG TTAACCTTTC CATTCTCAAA TTCCTCGGCT TGAACAAAC CTTCAAAAAT      360
GCCCTGACTA CTCTGCCGAT GGGCGGTGGT AAAGGCGGCA GCGATTTCGA TCCGAAAGGA     420
AAAAGCGAAG GTGAAGTGAT GCGTTTTTGC CAGGCGCTGA TGACTGAACT GTATCGCCAC     480
CTGGGCGCGG ATACCGACGT TCCGGCAGGT GATATCGGGG TTGGTGGTCG TGAAGTCGGC     540
TTTATGGCGG GGATGATGAA AAAGCTCTCC AACAATACCG CCTGCGTCTT CACCGGTAAG     600
GGCCTTTCAT TTGGCGGCAG TCTTATTCGC CCGGAAGCTA CCGGCTACGG TCTGGTTTAT     660
TTCACAGAAG CAATGCTAAA ACGCCACGGT ATGGGTTTTG AAGGGATGCG CGTTTCCGTT     720
TCTGGCTCCG GCAACGTCGC CCAGTACGCT ATCGAAAAAG CGATGGAATT TGGTGCTCGT     780
GTGATCACTG CGTCAGACTC CAGCGGCACT GTAGTTGATG AAAGCGGATT CACGAAAGAG     840
AAACTGGCAC GTCTTATCGA AATCAAAGCC AGCCGCGATG GTCGAGTGGC AGATTACGCC     900
AAAGAATTTG GTCTGGTCTA TCTCGAAGGC CAACAGCCGT GGTCTCTACC GGTTGATATC     960
GCCCTGCCTT GCGCCACCCA GAATGAACTG GATGTTGACG CCGCGCATCA GCTTATCGCT    1020
AATGGCGTTA AAGCCGTCGC CGAAGGGGCA AATATGCCGA CCACCATCGA AGCGACTGAA    1080
CTGTTCCAGC AGGCAGGCGT ACTATTTGCA CCGGGTAAAG CGGCTAATGC TGGTGGCGTC    1140
GCTACATCGG GCCTGGAAAT GGCACAAAAC GCTGCGCGCC TGGGCTGGAA AGCCGAGAAA    1200
GTTGACGCAC GTTTGCATCA CATCATGCTG GATATCCACC ATGCCTGTGT TGACCATGGT    1260
GGTGAAGGTG AGCAAACCAA CTACGTGCAG GGCGCGAACA TTGCCGGTTT TGTGAAGGTT    1320
```

```
GCCGATGCGA TGCTGGCGCA GGGTGTGATT TAAGTTGTAA ATGCCTGATG GCGCTACGCT      1380

TATCAGGCCT ACAAATGGGC ACAATTCATT GCAGTTACGC TCTAATGTAG GCCGGGCAAG      1440

CGCAGCGCCC CCGGCAAAAT TTCAGGCGTT TATGAGTATT TAAGAGCTC                  1489
```

(2) INFORMATION FOR SEQ ID NO:13:

(i) SEQUENCE CHARACTERISTICS:
        (A) LENGTH: 1482 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
GCATGCATCA GACATATTCT CTGGAGTCAT TCCTCAACCA TGTCCAAAAG CGCGACCCGA        60

ATCAAACCGA GTTCGCGCAA GCCGTTCGTG AAGTAATGAC CACACTCTGG CCTTTTCTTG       120

AACAAAATCC AAAATATCGC CAGATGTCAT TACTGGAGCG TCTGGTTGAA CCGGAGCGCG       180

TGATCCAGTT TCGCGTGGTA TGGGTTGATG ATCGCAACCA GATACAGGTC AACCGTGCAT       240

GGCGTGTGCA GTTCAGCTCT GCCATCGGCC CGTACAAAGG CGGTATGCGC TTCCATCCGT       300

CAGTTAACCT TTCCATTCTC AAATTCCTCG GCTTTGAACA AACCTTCAAA AATGCCCTGA       360

CTACTCTGCC GATGGGCGGT GGTAAAGGCG GCAGCGATTT CGATCCGAAA GGAAAAAGCG       420

AAGGTGAAGT GATGCGTTTT TGCCAGGCGC TGATGACTGA ACTGTATCGC CACCTGGGCG       480

CGGATACCGA CGTTCCGGCA GGTGATATCG GGGTTGGTGG TCGTGAAGTC GGCTTTATGG       540

CGGGGATGAT GAAAAAGCTC TCCAACAATA CCGCCTGCGT CTTCACCGGT AAGGGCCTTT       600

CATTTGGCGG CAGTCTTATT CGCCCGGAAG CTACCGGCTA CGGTCTGGTT TATTTCACAG       660

AAGCAATGCT AAAACGCCAC GGTATGGGTT TTGAAGGGAT GCGCGTTTCC GTTTCTGGCT       720

CCGGCAACGT CGCCCAGTAC GCTATCGAAA AAGCGATGGA ATTTGGTGCT CGTGTGATCA       780

CTGCGTCAGA CTCCAGCGGC ACTGTAGTTG ATGAAAGCGG ATTCACGAAA GAGAAACTGG       840

CACGTCTTAT CGAAATCAAA GCCAGCCGCG ATGGTCGAGT GGCAGATTAC GCCAAAGAAT       900

TTGGTCTGGT CTATCTCGAA GGCCAACAGC CGTGGTCTCT ACCGGTTGAT ATCGCCCTGC       960

CTTGCGCCAC CCAGAATGAA CTGGATGTTG ACGCCGCGCA TCAGCTTATC GCTAATGGCG      1020

TTAAAGCCGT CGCCGAAGGG GCAAATATGC CGACCACCAT CGAAGCGACT GAACTGTTCC      1080

AGCAGGCAGG CGTACTATTT GCACCGGGTA AAGCGGCTAA TGCTGGTGGC GTCGCTACAT      1140

CGGGCCTGGA AATGGCACAA AACGCTGCGC GCCTGGGCTG GAAAGCCGAG AAAGTTGACG      1200

CACGTTTGCA TCACATCATG CTGGATATCC ACCATGCCTG TGTTGACCAT GGTGGTGAAG      1260

GTGAGCAAAC CAACTACGTG CAGGGCGCGA ACATTGCCGG TTTTGTGAAG GTTGCCGATG      1320

CGATGCTGGC GCAGGGTGTG ATTTAAGTTG TAAATGCCTG ATGGCGCTAC GCTTATCAGG      1380

CCTACAAATG GCACAATTC ATTGCAGTTA CGCTCTAATG TAGGCCGGGC AAGCGCAGCG       1440

CCCCCGGCAA AATTTCAGGC GTTTATGAGT ATTTAAGAGC TC                        1482
```

(2) INFORMATION FOR SEQ ID NO:14:

(i) SEQUENCE CHARACTERISTICS:
        (A) LENGTH: 1501 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

| | | | | | |
|---|---|---|---|---|---|
| CTGCAGGTCG | ACTCTAGAAC | AATGGATCAG | ACATATTCTC | TGGAGTCATT | CCTCAACCAT | 60 |
| GTCCAAAAGC | GCGACCCGAA | TCAAACCGAG | TTCGCGCAAG | CCGTTCGTGA | AGTAATGACC | 120 |
| ACACTCTGGC | CTTTTCTTGA | ACAAAATCCA | AAATATCGCC | AGATGTCATT | ACTGGAGCGT | 180 |
| CTGGTTGAAC | CGGAGCGCGT | GATCCAGTTT | CGCGTGGTAT | GGGTTGATGA | TCGCAACCAG | 240 |
| ATACAGGTCA | ACCGTGCATG | GCGTGTGCAG | TTCAGCTCTG | CCATCGGCCC | GTACAAAGGC | 300 |
| GGTATGCGCT | TCCATCCGTC | AGTTAACCTT | TCCATTCTCA | AATTCCTCGG | CTTTGAACAA | 360 |
| ACCTTCAAAA | ATGCCCTGAC | TACTCTGCCG | ATGGGCGGTG | GTAAAGGCGG | CAGCGATTTC | 420 |
| GATCCGAAAG | GAAAAAGCGA | AGGTGAAGTG | ATGCGTTTTT | GCCAGGCGCT | GATGACTGAA | 480 |
| CTGTATCGCC | ACCTGGGCGC | GGATACCGAC | GTTCCGGCAG | GTGATATCGG | GGTTGGTGGT | 540 |
| CGTGAAGTCG | GCTTTATGGC | GGGGATGATG | AAAAAGCTCT | CCAACAATAC | CGCCTGCGTC | 600 |
| TTCACCGGTA | AGGGCCTTTC | ATTTGGCGGC | AGTCTTATTC | GCCCGGAAGC | TACCGGCTAC | 660 |
| GGTCTGGTTT | ATTTCACAGA | AGCAATGCTA | AAACGCCACG | GTATGGGTTT | TGAAGGGATG | 720 |
| CGCGTTTCCG | TTTCTGGCTC | CGGCAACGTC | GCCCAGTACG | CTATCGAAAA | AGCGATGGAA | 780 |
| TTTGGTGCTC | GTGTGATCAC | TGCGTCAGAC | TCCAGCGGCA | CTGTAGTTGA | TGAAAGCGGA | 840 |
| TTCACGAAAG | AGAAACTGGC | ACGTCTTATC | GAAATCAAAG | CCAGCCGCGA | TGGTCGAGTG | 900 |
| GCAGATTACG | CCAAAGAATT | TGGTCTGGTC | TATCTCGAAG | GCCAACAGCC | GTGGTCTCTA | 960 |
| CCGGTTGATA | TCGCCCTGCC | TTGCGCCACC | CAGAATGAAC | TGGATGTTGA | CGCCGCGCAT | 1020 |
| CAGCTTATCG | CTAATGGCGT | TAAAGCCGTC | GCCGAAGGGG | CAAATATGCC | GACCACCATC | 1080 |
| GAAGCGACTG | AACTGTTCCA | GCAGGCAGGC | GTACTATTTG | CACCGGGTAA | AGCGGCTAAT | 1140 |
| GCTGGTGGCG | TCGCTACATC | GGGCCTGGAA | ATGGCACAAA | ACGCTGCGCG | CCTGGGCTGG | 1200 |
| AAAGCCGAGA | AGTTGACGC | ACGTTTGCAT | CACATCATGC | TGGATATCCA | CCATGCCTGT | 1260 |
| GTTGACCATG | GTGGTGAAGG | TGAGCAAACC | AACTACGTGC | AGGGCGCGAA | CATTGCCGGT | 1320 |
| TTTGTGAAGG | TTGCCGATGC | GATGCTGGCG | CAGGGTGTGA | TTTAAGTTGT | AAATGCCTGA | 1380 |
| TGGCGCTACG | CTTATCAGGC | CTACAAATGG | CACAATTCA | TTGCAGTTAC | GCTCTAATGT | 1440 |
| AGGCCGGGCA | AGCGCAGCGC | CCCCGGCAAA | ATTTCAGGCG | TTTATGAGTA | TTTAAGAGCT | 1500 |
| C | | | | | | 1501 |

(2) INFORMATION FOR SEQ ID NO:15:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AATTCGAACC CCTTCGCATG                                            20

(2) INFORMATION FOR SEQ ID NO:16:

(i) SEQUENCE CHARACTERISTICS:
        (A) LENGTH: 12 bases
        (B) TYPE: nucleic acid
        (C) STRANDEDNESS: single
        (D) TOPOLOGY: linear -continued (ii) MOLECULE TYPE: DNA (xi) SEQUENCE DESCRIPTION: SEQ ID NO:16:

CGAAGGGGTT CG                                                                12

(2) INFORMATION FOR SEQ ID NO:17:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGTTTTATAT GCATGCATCA GACATATTC                                              29